US012788330B2

(12) United States Patent
Olsen

(10) Patent No.: US 12,788,330 B2
(45) Date of Patent: Nov. 10, 2026

(54) CONFIGURABLE PATIENT MONITORING SYSTEM

(71) Applicant: Masimo Corporation, Irvine, CA (US)

(72) Inventor: Gregory A. Olsen, Trabuco Canyon, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 15/339,639

(22) Filed: Oct. 31, 2016

(65) Prior Publication Data

US 2017/0143281 A1 May 25, 2017

Related U.S. Application Data

(63) Continuation of application No. 13/762,751, filed on Feb. 8, 2013, now Pat. No. 9,480,435.

(60) Provisional application No. 61/597,140, filed on Feb. 9, 2012.

(51) Int. Cl.

| | |
|---|---|
| ***A61B 5/00*** | (2006.01) |
| ***A61B 5/01*** | (2006.01) |
| ***A61B 5/0205*** | (2006.01) |
| ***A61B 5/021*** | (2006.01) |
| ***A61B 5/024*** | (2006.01) |
| ***A61B 5/026*** | (2006.01) |
| ***A61B 5/08*** | (2006.01) |
| ***A61B 5/145*** | (2006.01) |
| ***A61B 5/1455*** | (2006.01) |
| ***G06T 11/20*** | (2006.01) |
| ***G06T 13/80*** | (2011.01) |
| ***G16H 40/63*** | (2018.01) |

(52) U.S. Cl.

CPC ............ *A61B 5/743* (2013.01); *A61B 5/0008* (2013.01); *A61B 5/02055* (2013.01); *A61B 5/0261* (2013.01); *A61B 5/14532* (2013.01); *A61B 5/14546* (2013.01); *A61B 5/14552* (2013.01); *A61B 5/7282* (2013.01); *A61B 5/7405* (2013.01); *A61B 5/742* (2013.01); *A61B 5/746* (2013.01); *G06T 11/206* (2013.01); *G16H 40/63* (2018.01); *A61B 5/01* (2013.01); *A61B 5/021* (2013.01); *A61B 5/02416* (2013.01); *A61B 5/0816* (2013.01); *A61B 5/14551* (2013.01); *A61B 5/744* (2013.01); *G06T 13/80* (2013.01); *G06T 2219/2016* (2013.01)

(58) Field of Classification Search

None

See application file for complete search history.

(56) References Cited

U.S. PATENT DOCUMENTS

| | | | |
|---|---|---|---|
| 4,300,548 | A | 11/1981 | Jones |
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| 5,436,499 | A | 7/1995 | Namavar et al. |
| D361,840 | S | 8/1995 | Savage et al. |
| D362,063 | S | 9/1995 | Savage et al. |
| 5,452,717 | A | 9/1995 | Branigan et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,561,275 | A | 10/1996 | Savage et al. |
| 5,562,002 | A | 10/1996 | Lalin |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,685,299 | A | 11/1997 | Diab et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |

(Continued)

OTHER PUBLICATIONS

US 8,845,543 B2, 09/2014, Diab et al. (withdrawn)
US 2022/0192529 A1, 06/2022, Al-Ali et al. (withdrawn)
US 2024/0016391 A1, 01/2024, Lapotko et al. (withdrawn)
Marcus (Readings in Human-Computer Interaction, 2nd Edition, Interactive Technologies, 1995, pp. 425-441) (Year: 1995).*
Rodbard et al. (Journal of Diabetes Science and Technology vol. 3, Issue 6, Nov. 2009, pp. 1388-1394) (Year: 2009).*
Keim et al. (AVI '04: Proceedings of the working conference on Advanced visual interfaces, May 2004, pp. 179-182). (Year: 2004).*

(Continued)

*Primary Examiner* — Pablo S Whaley
(74) *Attorney, Agent, or Firm* — Knobbe, Martens, Olson & Bear, LLP

(57) ABSTRACT

A patient monitoring system can display one or more configurable health monitors on a configurable user interface. The health indicators are configured to display a physiological signal from a patient. The patient monitoring system can calculate ranges of values for the health indicator that correspond to a status of the patient. The health indicators can display different outputs based on the value of the physiological signal.

18 Claims, 5 Drawing Sheets

(56) References Cited

U.S. PATENT DOCUMENTS

| | | | |
|---|---|---|---|
| 5,750,994 | A | 5/1998 | Schlager |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab et al. |
| 6,010,937 | A | 1/2000 | Karam et al. |
| 6,011,986 | A | 1/2000 | Diab et al. |
| 6,027,452 | A | 2/2000 | Flaherty et al. |
| 6,036,642 | A | 3/2000 | Diab et al. |
| 6,040,578 | A | 3/2000 | Malin et al. |
| 6,045,509 | A | 4/2000 | Caro et al. |
| 6,066,204 | A | 5/2000 | Haven |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,115,673 | A | 9/2000 | Malin et al. |
| 6,124,597 | A | 9/2000 | Shehada |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,323,852 | B1 | 11/2001 | Blower et al. |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,373 | B1 | 6/2002 | Garside et al. |
| 6,415,167 | B1 | 7/2002 | Blank et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kiani et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,738,652 | B2 | 5/2004 | Mattu et al. |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,788,965 | B2 | 9/2004 | Ruchti et al. |
| 6,792,300 | B1 | 9/2004 | Diab et al. |
| 6,813,511 | B2 | 11/2004 | Diab et al. |
| 6,816,241 | B2 | 11/2004 | Grubisic |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,876,931 | B2 | 4/2005 | Lorenz et al. |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,956,649 | B2 | 10/2005 | Acosta et al. |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,990,364 | B2 | 1/2006 | Ruchti et al. |
| 6,993,371 | B2 | 1/2006 | Kiani et al. |
| 6,996,427 | B2 | 2/2006 | Ali et al. |
| 6,998,247 | B2 | 2/2006 | Monfre et al. |

(56) References Cited

U.S. PATENT DOCUMENTS

| | | | |
|---|---|---|---|
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,048,687 | B1 | 5/2006 | Reuss et al. |
| 7,067,893 | B2 | 6/2006 | Mills et al. |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| D529,616 | S | 10/2006 | Deros et al. |
| 7,132,641 | B2 | 11/2006 | Schulz et al. |
| 7,133,710 | B2 | 11/2006 | Acosta et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |
| 7,222,308 | B2 | 5/2007 | Sauermann et al. |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |
| 7,371,981 | B2 | 5/2008 | Abdul-Hafiz |
| 7,373,193 | B2 | 5/2008 | Al-Ali et al. |
| 7,373,194 | B2 | 5/2008 | Weber et al. |
| 7,376,453 | B1 | 5/2008 | Diab et al. |
| 7,377,794 | B2 | 5/2008 | Ali et al. |
| 7,377,899 | B2 | 5/2008 | Weber et al. |
| 7,383,070 | B2 | 6/2008 | Diab et al. |
| 7,395,158 | B2 | 7/2008 | Monfre et al. |
| 7,415,297 | B2 | 8/2008 | Al-Ali et al. |
| 7,428,432 | B2 | 9/2008 | Ali et al. |
| 7,438,683 | B2 | 10/2008 | Al-Ali et al. |
| 7,440,787 | B2 | 10/2008 | Diab |
| 7,454,240 | B2 | 11/2008 | Diab et al. |
| 7,467,002 | B2 | 12/2008 | Weber et al. |
| 7,469,157 | B2 | 12/2008 | Diab et al. |
| 7,471,969 | B2 | 12/2008 | Diab et al. |
| 7,471,971 | B2 | 12/2008 | Diab et al. |
| 7,483,729 | B2 | 1/2009 | Al-Ali et al. |
| 7,483,730 | B2 | 1/2009 | Diab et al. |
| 7,489,958 | B2 | 2/2009 | Diab et al. |
| 7,496,391 | B2 | 2/2009 | Diab et al. |
| 7,496,393 | B2 | 2/2009 | Diab et al. |
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,514,725 | B2 | 4/2009 | Wojtczuk et al. |
| 7,519,406 | B2 | 4/2009 | Blank et al. |
| 7,526,328 | B2 | 4/2009 | Diab et al. |
| D592,507 | S | 5/2009 | Wachman et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,593,230 | B2 | 9/2009 | Abul-Haj et al. |
| 7,596,398 | B2 | 9/2009 | Al-Ali et al. |
| 7,606,608 | B2 | 10/2009 | Blank et al. |
| 7,618,375 | B2 | 11/2009 | Flaherty |
| 7,620,674 | B2 | 11/2009 | Ruchti et al. |
| D606,659 | S | 12/2009 | Kiani et al. |
| 7,629,039 | B2 | 12/2009 | Eckerbom et al. |
| 7,640,140 | B2 | 12/2009 | Ruchti et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| 7,697,966 | B2 | 4/2010 | Monfre et al. |
| 7,698,105 | B2 | 4/2010 | Ruchti et al. |
| RE41,317 | E | 5/2010 | Parker |
| RE41,333 | E | 5/2010 | Blank et al. |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| 7,801,581 | B2 | 9/2010 | Diab |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,899,518 | B2 | 3/2011 | Trepagnier et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| 8,092,379 | B2 | 1/2012 | Baker, Jr. |
| RE43,169 | E | 2/2012 | Parker |

(56) References Cited

U.S. PATENT DOCUMENTS 8,118,620 B2 2/2012 Al-Ali et al.
8,126,528 B2 2/2012 Diab et al.
8,128,572 B2 3/2012 Diab et al.
8,130,105 B2 3/2012 Al-Ali et al.
8,145,287 B2 3/2012 Diab et al.
8,150,487 B2 4/2012 Diab et al.
8,175,672 B2 5/2012 Parker
8,180,420 B2 5/2012 Diab et al.
8,182,443 B1 5/2012 Kiani
8,185,180 B2 5/2012 Diab et al.
8,190,223 B2 5/2012 Al-Ali et al.
8,190,227 B2 5/2012 Diab et al.
8,203,438 B2 6/2012 Kiani et al.
8,203,704 B2 6/2012 Merritt et al.
8,204,566 B2 6/2012 Schurman et al.
8,219,172 B2 7/2012 Schurman et al.
8,224,411 B2 7/2012 Al-Ali et al.
8,228,181 B2 7/2012 Al-Ali
8,229,532 B2 7/2012 Davis
8,229,533 B2 7/2012 Diab et al.
8,233,955 B2 7/2012 Al-Ali et al.
8,244,325 B2 8/2012 Al-Ali et al.
8,251,903 B2 8/2012 LeBoeuf et al.
8,255,026 B1 8/2012 Al-Ali
8,255,027 B2 8/2012 Al-Ali et al.
8,255,028 B2 8/2012 Al-Ali et al.
8,260,577 B2 9/2012 Weber et al.
8,265,723 B1 9/2012 McHale et al.
8,274,360 B2 9/2012 Sampath et al.
8,280,473 B2 10/2012 Al-Ali
8,290,559 B2 10/2012 Shariati et al.
8,301,217 B2 10/2012 Al-Ali et al.
8,306,596 B2 11/2012 Schurman et al.
8,310,336 B2 11/2012 Muhsin et al.
8,315,683 B2 11/2012 Al-Ali et al.
RE43,860 E 12/2012 Parker
8,337,403 B2 12/2012 Al-Ali et al.
8,346,330 B2 1/2013 Lamego
8,353,842 B2 1/2013 Al-Ali et al.
8,355,766 B2 1/2013 MacNeish, III et al.
8,359,080 B2 1/2013 Diab et al.
8,364,223 B2 1/2013 Al-Ali et al.
8,364,226 B2 1/2013 Diab et al.
8,374,665 B2 2/2013 Lamego
8,385,995 B2 2/2013 Al-Ali et al.
8,385,996 B2 2/2013 Smith et al.
8,388,353 B2 3/2013 Kiani
8,399,822 B2 3/2013 Al-Ali
8,401,602 B2 3/2013 Kiani
8,405,608 B2 3/2013 Al-Ali et al.
8,414,499 B2 4/2013 Al-Ali et al.
8,418,524 B2 4/2013 Al-Ali
8,423,106 B2 4/2013 Lamego et al.
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,703 B2 6/2013 Al-Ali
8,457,707 B2 6/2013 Kiani
8,463,349 B2 6/2013 Diab et al.
8,466,286 B2 6/2013 Bellot et al.
8,471,713 B2 6/2013 Poeze et al.
8,473,020 B2 6/2013 Kiani et al.
8,483,787 B2 7/2013 Al-Ali et al.
8,489,364 B2 7/2013 Weber et al.
8,498,684 B2 7/2013 Weber et al.
8,504,128 B2 8/2013 Blank et al.
8,509,867 B2 8/2013 Workman et al.
8,515,509 B2 8/2013 Bruinsma et al.
8,523,781 B2 9/2013 Al-Ali
8,529,301 B2 9/2013 Al-Ali et al.
8,532,727 B2 9/2013 Ali et al.
8,532,728 B2 9/2013 Diab et al.
D692,145 S 10/2013 Al-Ali et al.
8,547,209 B2 10/2013 Kiani et al.
8,548,548 B2 10/2013 Al-Ali
8,548,549 B2 10/2013 Schurman et al.
8,548,550 B2 10/2013 Al-Ali et al.
8,560,032 B2 10/2013 Al-Ali et al.
8,560,034 B1 10/2013 Diab et al.
8,570,167 B2 10/2013 Al-Ali
8,570,503 B2 10/2013 Vo et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,581,732 B2 11/2013 Al-Ali et al.
8,584,345 B2 11/2013 Al-Ali et al.
8,588,880 B2 11/2013 Abdul-Hafiz et al.
8,600,467 B2 12/2013 Al-Ali et al.
8,606,342 B2 12/2013 Diab
8,626,255 B2 1/2014 Al-Ali et al.
8,630,691 B2 1/2014 Lamego et al.
8,634,889 B2 1/2014 Al-Ali et al.
8,641,631 B2 2/2014 Sierra et al.
8,652,060 B2 2/2014 Al-Ali
8,663,107 B2 3/2014 Kiani
8,666,468 B1 3/2014 Al-Ali
8,667,967 B2 3/2014 Al-Ali et al.
8,670,811 B2 3/2014 O'Reilly
8,670,814 B2 3/2014 Diab et al.
8,676,286 B2 3/2014 Weber et al.
8,682,407 B2 3/2014 Al-Ali
RE44,823 E 4/2014 Parker
RE44,875 E 4/2014 Kiani et al.
8,688,183 B2 4/2014 Bruinsma et al.
8,690,799 B2 4/2014 Telfort et al.
8,700,112 B2 4/2014 Kiani
8,702,627 B2 4/2014 Telfort et al.
8,706,179 B2 4/2014 Parker
8,712,494 B1 4/2014 MacNeish, III et al.
8,715,206 B2 5/2014 Telfort et al.
8,718,735 B2 5/2014 Lamego et al.
8,718,737 B2 5/2014 Diab et al.
8,718,738 B2 5/2014 Blank et al.
8,720,249 B2 5/2014 Al-Ali
8,721,541 B2 5/2014 Al-Ali et al.
8,721,542 B2 5/2014 Al-Ali et al.
8,723,677 B1 5/2014 Kiani
8,740,792 B1 6/2014 Kiani et al.
8,754,776 B2 6/2014 Poeze et al.
8,755,535 B2 6/2014 Telfort et al.
8,755,856 B2 6/2014 Diab et al.
8,755,872 B1 6/2014 Marinow
8,761,850 B2 6/2014 Lamego
8,764,671 B2 7/2014 Kiani
8,768,423 B2 7/2014 Shakespeare et al.
8,771,204 B2 7/2014 Telfort et al.
8,773,259 B2 7/2014 Judy et al.
8,777,634 B2 7/2014 Kiani et al.
8,781,543 B2 7/2014 Diab et al.
8,781,544 B2 7/2014 Al-Ali et al.
8,781,549 B2 7/2014 Al-Ali et al.
8,788,003 B2 7/2014 Schurman et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,831,700 B2 9/2014 Schurman et al.
8,840,549 B2 9/2014 Al-Ali et al.
8,847,740 B2 9/2014 Kiani et al.
8,849,365 B2 9/2014 Smith et al.
8,852,094 B2 10/2014 Al-Ali et al.
8,852,994 B2 10/2014 Wojtczuk et al.
8,868,147 B2 10/2014 Stippick et al.
8,868,150 B2 10/2014 Al-Ali et al.
8,870,792 B2 10/2014 Al-Ali et al.
8,886,271 B2 11/2014 Kiani et al.
8,888,539 B2 11/2014 Al-Ali et al.
8,888,708 B2 11/2014 Diab et al.
8,892,180 B2 11/2014 Weber et al.
8,897,847 B2 11/2014 Al-Ali
8,909,310 B2 12/2014 Lamego et al.

(56) References Cited

U.S. PATENT DOCUMENTS

| | | | |
|---|---|---|---|
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,961,415 | B2 | 2/2015 | LeBoeuf et al. |
| 8,965,471 | B2 | 2/2015 | Lamego |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| 9,028,429 | B2 | 5/2015 | Telfort et al. |
| 9,037,207 | B2 | 5/2015 | Al-Ali et al. |
| 9,060,721 | B2 | 6/2015 | Reichgott et al. |
| 9,066,666 | B2 | 6/2015 | Kiani |
| 9,066,680 | B1 | 6/2015 | Al-Ali et al. |
| 9,072,474 | B2 | 7/2015 | Al-Ali et al. |
| 9,078,560 | B2 | 7/2015 | Schurman et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Al-Ali |
| 9,113,832 | B2 | 8/2015 | Al-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Al-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,072 | B2 | 12/2015 | Kiani |
| 9,211,095 | B1 | 12/2015 | Al-Ali |
| 9,218,454 | B2 | 12/2015 | Kiani et al. |
| 9,220,409 | B2 | 12/2015 | Lisogurski |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,267,572 | B2 | 2/2016 | Barker et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,341,565 | B2 | 5/2016 | Lamego et al. |
| 9,351,673 | B2 | 5/2016 | Diab et al. |
| 9,351,675 | B2 | 5/2016 | Al-Ali et al. |
| 9,364,181 | B2 | 6/2016 | Kiani et al. |
| 9,368,671 | B2 | 6/2016 | Wojtczuk et al. |
| 9,370,325 | B2 | 6/2016 | Al-Ali et al. |
| 9,370,326 | B2 | 6/2016 | McHale et al. |
| 9,370,335 | B2 | 6/2016 | Al-ali et al. |
| 9,375,185 | B2 | 6/2016 | Ali et al. |
| 9,386,953 | B2 | 7/2016 | Al-Ali |
| 9,386,961 | B2 | 7/2016 | Al-Ali et al. |
| 9,392,945 | B2 | 7/2016 | Al-Ali et al. |
| 9,397,448 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,466,919 | B2 | 10/2016 | Kiani et al. |
| 9,474,474 | B2 | 10/2016 | Lamego et al. |
| 9,480,422 | B2 | 11/2016 | Al-Ali |
| 9,480,435 | B2 | 11/2016 | Olsen |
| 9,492,110 | B2 | 11/2016 | Al-Ali et al. |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,538,949 | B2 | 1/2017 | Al-Ali et al. |
| 9,538,980 | B2 | 1/2017 | Telfort et al. |
| 9,549,696 | B2 | 1/2017 | Lamego et al. |
| 9,554,737 | B2 | 1/2017 | Schurman et al. |
| 9,560,996 | B2 | 2/2017 | Kiani |
| 9,560,998 | B2 | 2/2017 | Al-Ali et al. |
| 9,566,019 | B2 | 2/2017 | Al-Ali et al. |
| 9,579,039 | B2 | 2/2017 | Jansen et al. |
| 9,591,975 | B2 | 3/2017 | Dalvi et al. |
| 9,622,692 | B2 | 4/2017 | Lamego et al. |
| 9,622,693 | B2 | 4/2017 | Diab |
| D788,312 | S | 5/2017 | Al-Ali et al. |
| 9,636,055 | B2 | 5/2017 | Al-Ali et al. |
| 9,636,056 | B2 | 5/2017 | Al-Ali |
| 9,649,054 | B2 | 5/2017 | Lamego et al. |
| 9,662,052 | B2 | 5/2017 | Al-Ali et al. |
| 9,668,679 | B2 | 6/2017 | Schurman et al. |
| 9,668,680 | B2 | 6/2017 | Bruinsma et al. |
| 9,668,703 | B2 | 6/2017 | Al-Ali |
| 9,675,286 | B2 | 6/2017 | Diab |
| 9,687,160 | B2 | 6/2017 | Kiani |
| 9,693,719 | B2 | 7/2017 | Al-Ali et al. |
| 9,693,737 | B2 | 7/2017 | Al-Ali |
| 9,697,928 | B2 | 7/2017 | Al-Ali et al. |
| 9,717,425 | B2 | 8/2017 | Kiani et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,730,640 | B2 | 8/2017 | Diab et al. |
| 9,743,887 | B2 | 8/2017 | Al-Ali et al. |
| 9,749,232 | B2 | 8/2017 | Sampath et al. |
| 9,750,442 | B2 | 9/2017 | Olsen |
| 9,750,443 | B2 | 9/2017 | Smith et al. |
| 9,750,461 | B1 | 9/2017 | Telfort |
| 9,775,545 | B2 | 10/2017 | Al-Ali et al. |
| 9,775,546 | B2 | 10/2017 | Diab et al. |
| 9,775,570 | B2 | 10/2017 | Al-Ali |
| 9,778,079 | B1 | 10/2017 | Al-Ali et al. |
| 9,782,077 | B2 | 10/2017 | Lamego et al. |
| 9,782,110 | B2 | 10/2017 | Kiani |
| 9,787,568 | B2 | 10/2017 | Lamego et al. |
| 9,788,735 | B2 | 10/2017 | Al-Ali |
| 9,788,768 | B2 | 10/2017 | Al-Ali et al. |
| 9,795,300 | B2 | 10/2017 | Al-Ali |
| 9,795,310 | B2 | 10/2017 | Al-Ali |
| 9,795,358 | B2 | 10/2017 | Telfort et al. |
| 9,795,739 | B2 | 10/2017 | Al-Ali et al. |
| 9,801,556 | B2 | 10/2017 | Kiani |
| 9,801,588 | B2 | 10/2017 | Weber et al. |
| 9,808,188 | B1 | 11/2017 | Perea et al. |
| 9,814,418 | B2 | 11/2017 | Weber et al. |
| 9,820,691 | B2 | 11/2017 | Kiani |
| 9,833,152 | B2 | 12/2017 | Kiani et al. |
| 9,833,180 | B2 | 12/2017 | Shakespeare et al. |
| 9,839,379 | B2 | 12/2017 | Al-Ali et al. |
| 9,839,381 | B1 | 12/2017 | Weber et al. |
| 9,847,002 | B2 | 12/2017 | Kiani et al. |
| 9,847,749 | B2 | 12/2017 | Kiani et al. |
| 9,848,800 | B1 | 12/2017 | Lee et al. |
| 9,848,806 | B2 | 12/2017 | Al-Ali et al. |
| 9,848,807 | B2 | 12/2017 | Lamego |
| 9,861,298 | B2 | 1/2018 | Eckerbom et al. |

(56) References Cited

U.S. PATENT DOCUMENTS

| | | | |
|---|---|---|---|
| 9,861,304 | B2 | 1/2018 | Al-Ali et al. |
| 9,861,305 | B1 | 1/2018 | Weber et al. |
| 9,867,578 | B2 | 1/2018 | Al-Ali et al. |
| 9,872,623 | B2 | 1/2018 | Al-Ali |
| 9,876,320 | B2 | 1/2018 | Coverston et al. |
| 9,877,650 | B2 | 1/2018 | Muhsin et al. |
| 9,877,686 | B2 | 1/2018 | Al-Ali et al. |
| 9,891,079 | B2 | 2/2018 | Dalvi |
| 9,895,107 | B2 | 2/2018 | Al-Ali et al. |
| 9,913,617 | B2 | 3/2018 | Al-Ali et al. |
| 9,924,893 | B2 | 3/2018 | Schurman et al. |
| 9,924,897 | B1 | 3/2018 | Abdul-Hafiz |
| 9,936,917 | B2 | 4/2018 | Poeze et al. |
| 9,943,269 | B2 | 4/2018 | Muhsin et al. |
| 9,949,676 | B2 | 4/2018 | Al-Ali |
| 9,955,937 | B2 | 5/2018 | Telfort |
| 9,965,946 | B2 | 5/2018 | Al-Ali |
| 9,980,667 | B2 | 5/2018 | Kiani et al. |
| D820,865 | S | 6/2018 | Muhsin et al. |
| 9,986,919 | B2 | 6/2018 | Lamego et al. |
| 9,986,952 | B2 | 6/2018 | Dalvi et al. |
| 9,989,560 | B2 | 6/2018 | Poeze et al. |
| 9,993,207 | B2 | 6/2018 | Al-Ali et al. |
| 10,007,758 | B2 | 6/2018 | Al-Ali et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,032,002 | B2 | 7/2018 | Kiani et al. |
| 10,039,482 | B2 | 8/2018 | Al-Ali et al. |
| 10,052,037 | B2 | 8/2018 | Kinast et al. |
| 10,058,275 | B2 | 8/2018 | Al-Ali et al. |
| 10,064,562 | B2 | 9/2018 | Al-Ali |
| 10,076,282 | B2 | 9/2018 | LeBoeuf et al. |
| 10,086,138 | B1 | 10/2018 | Novak, Jr. |
| 10,092,200 | B2 | 10/2018 | Al-Ali et al. |
| 10,092,249 | B2 | 10/2018 | Kiani et al. |
| 10,098,550 | B2 | 10/2018 | Al-Ali et al. |
| 10,098,591 | B2 | 10/2018 | Al-Ali et al. |
| 10,098,610 | B2 | 10/2018 | Al-Ali et al. |
| 10,111,591 | B2 | 10/2018 | Dyell et al. |
| D833,624 | S | 11/2018 | DeJong et al. |
| 10,123,726 | B2 | 11/2018 | Al-Ali et al. |
| 10,123,729 | B2 | 11/2018 | Dyell et al. |
| 10,130,289 | B2 | 11/2018 | Al-Ali et al. |
| 10,130,291 | B2 | 11/2018 | Schurman et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,296 | B2 | 1/2019 | Al-Ali et al. |
| 10,188,331 | B1 | 1/2019 | Al-Ali et al. |
| 10,188,348 | B2 | 1/2019 | Kiani et al. |
| RE47,218 | E | 2/2019 | Ali-Ali |
| RE47,244 | E | 2/2019 | Kiani et al. |
| RE47,249 | E | 2/2019 | Kiani et al. |
| 10,194,847 | B2 | 2/2019 | Ai-Ali |
| 10,194,848 | B1 | 2/2019 | Kiani et al. |
| 10,201,298 | B2 | 2/2019 | Al-Ali et al. |
| 10,205,272 | B2 | 2/2019 | Kiani et al. |
| 10,205,291 | B2 | 2/2019 | Scruggs et al. |
| 10,213,108 | B2 | 2/2019 | Al-Ali |
| 10,219,706 | B2 | 3/2019 | Al-Ali |
| 10,219,746 | B2 | 3/2019 | McHale et al. |
| 10,226,187 | B2 | 3/2019 | Al-Ali et al. |
| 10,226,576 | B2 | 3/2019 | Kiani |
| 10,231,657 | B2 | 3/2019 | Al-Ali et al. |
| 10,231,670 | B2 | 3/2019 | Blank et al. |
| 10,231,676 | B2 | 3/2019 | Al-Ali et al. |
| RE47,353 | E | 4/2019 | Kiani et al. |
| 10,251,585 | B2 | 4/2019 | Al-Ali et al. |
| 10,251,586 | B2 | 4/2019 | Lamego |
| 10,255,994 | B2 | 4/2019 | Sampath et al. |
| 10,258,265 | B1 | 4/2019 | Poeze et al. |
| 10,258,266 | B1 | 4/2019 | Poeze et al. |
| 10,271,748 | B2 | 4/2019 | Al-Ali |
| 10,278,626 | B2 | 5/2019 | Schurman et al. |
| 10,278,648 | B2 | 5/2019 | Al-Ali et al. |
| 10,279,247 | B2 | 5/2019 | Kiani |
| 10,292,628 | B1 | 5/2019 | Poeze et al. |
| 10,292,657 | B2 | 5/2019 | Abdul-Hafiz et al. |
| 10,292,664 | B2 | 5/2019 | Al-Ali |
| 10,299,708 | B1 | 5/2019 | Poeze et al. |
| 10,299,709 | B2 | 5/2019 | Perea et al. |
| 10,299,720 | B2 | 5/2019 | Brown et al. |
| 10,305,775 | B2 | 5/2019 | Lamego et al. |
| 10,307,111 | B2 | 6/2019 | Muhsin et al. |
| 10,327,713 | B2 | 6/2019 | Barker et al. |
| 10,332,630 | B2 | 6/2019 | Al-Ali |
| 10,335,033 | B2 | 7/2019 | Al-Ali |
| 10,335,068 | B2 | 7/2019 | Poeze et al. |
| 10,335,072 | B2 | 7/2019 | Al-Ali et al. |
| 10,342,470 | B2 | 7/2019 | Al-Ali et al. |
| 10,342,487 | B2 | 7/2019 | Al-Ali et al. |
| 10,342,497 | B2 | 7/2019 | Al-Ali et al. |
| 10,349,895 | B2 | 7/2019 | Telfort et al. |
| 10,349,898 | B2 | 7/2019 | Al-Ali et al. |
| 10,354,504 | B2 | 7/2019 | Kiani et al. |
| 10,357,206 | B2 | 7/2019 | Weber et al. |
| 10,357,209 | B2 | 7/2019 | Al-Ali |
| 10,366,787 | B2 | 7/2019 | Sampath et al. |
| 10,368,787 | B2 | 8/2019 | Reichgott et al. |
| 10,376,190 | B1 | 8/2019 | Poeze et al. |
| 10,376,191 | B1 | 8/2019 | Poeze et al. |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| 10,398,320 | B2 | 9/2019 | Kiani et al. |
| 10,405,804 | B2 | 9/2019 | Al-Ali |
| 10,413,666 | B2 | 9/2019 | Al-Ali et al. |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,340 | B2 | 11/2019 | Telfort et al. |
| 10,471,159 | B1 | 11/2019 | Lapotko et al. |
| 10,505,311 | B2 | 12/2019 | Al-Ali et al. |
| 10,524,738 | B2 | 1/2020 | Olsen |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,555,678 | B2 | 2/2020 | Dalvi et al. |
| 10,568,553 | B2 | 2/2020 | O'Neil et al. |
| RE47,882 | E | 3/2020 | Al-Ali |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,729,402 | B2 | 8/2020 | Al-Ali et al. |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |

(56) References Cited

U.S. PATENT DOCUMENTS

| | | | |
|---|---|---|---|
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Ai-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,014,328 | B2 | 6/2024 | Wachman et al. |
| D1,036,293 | S | 7/2024 | Al-Ali |
| D1,037,462 | S | 7/2024 | Al-Ali et al. |
| 12,029,844 | B2 | 7/2024 | Pauley et al. |
| 12,048,534 | B2 | 7/2024 | Vo et al. |
| 12,064,217 | B2 | 8/2024 | Ahmed et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |
| 12,178,572 | B1 | 12/2024 | Pauley et al. |
| 12,178,581 | B2 | 12/2024 | Telfort et al. |
| 12,178,852 | B2 | 12/2024 | Kiani et al. |
| D1,057,159 | S | 1/2025 | DeJong et al. |
| D1,057,160 | S | 1/2025 | DeJong et al. |
| 12,198,790 | B1 | 1/2025 | Al-Ali |
| 12,200,421 | B2 | 1/2025 | Campbell et al. |
| 12,207,901 | B1 | 1/2025 | Lapotko et al. |
| D1,060,680 | S | 2/2025 | Al-Ali et al. |
| D1,061,585 | S | 2/2025 | Indorf |
| D1,063,893 | S | 2/2025 | DeJong et al. |
| 12,220,207 | B2 | 2/2025 | Telfort et al. |
| 12,235,941 | B2 | 2/2025 | Kiani et al. |
| 12,236,767 | B2 | 2/2025 | Muhsin |
| D1,066,244 | S | 3/2025 | Lim et al. |
| D1,066,672 | S | 3/2025 | Al-Ali et al. |
| D1,068,656 | S | 4/2025 | Trevisan et al. |
| D1,071,195 | S | 4/2025 | Seung |
| D1,072,836 | S | 4/2025 | Indorf |
| D1,072,837 | S | 4/2025 | Ahmed et al. |
| 12,272,445 | B1 | 4/2025 | Kiani |
| D1,078,689 | S | 6/2025 | Hwang |
| D1,079,020 | S | 6/2025 | Hwang |
| 12,336,796 | B2 | 6/2025 | Al-Ali |
| D1,083,653 | S | 7/2025 | DeJong et al. |
| D1,085,102 | S | 7/2025 | Indorf et al. |
| 12,362,596 | B2 | 7/2025 | Barker et al. |
| 12,390,114 | B2 | 8/2025 | Novak, Jr. et al. |
| D1,092,244 | S | 9/2025 | DeJong et al. |
| D1,093,406 | S | 9/2025 | Indorf et al. |
| D1,094,735 | S | 9/2025 | DeJong et al. |
| D1,095,288 | S | 9/2025 | Lim |
| D1,095,483 | S | 9/2025 | DeJong et al. |
| 12,433,524 | B2 | 10/2025 | Al-Ali et al. |
| 12,440,128 | B2 | 10/2025 | Al-Ali et al. |
| D1,102,622 | S | 11/2025 | Al-Ali et al. |
| 12,478,272 | B2 | 11/2025 | Telfort et al. |
| 12,478,293 | B1 | 11/2025 | Al-Ali et al. |
| D1,106,466 | S | 12/2025 | Avendaño et al. |

(56) References Cited

U.S. PATENT DOCUMENTS 12,495,967 B2 12/2025 Muhsin et al.
12,495,999 B2 12/2025 Al-Ali et al.
12,507,952 B2 12/2025 Al-Ali et al.
12,521,021 B2 1/2026 Al-Ali et al.
12,521,506 B2 1/2026 Yu et al.
12,538,084 B1 1/2026 Telfort et al.
12,539,046 B2 2/2026 Kiani
12,575,797 B2 3/2026 Olsen et al.
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0085039 A1 7/2002 Blower et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2006/0073719 A1 4/2006 Kiani
2006/0074321 A1 4/2006 Kouchi et al.
2006/0161054 A1 7/2006 Reuss et al.
2006/0189871 A1 8/2006 Al-Ali et al.
2007/0030137 A1 2/2007 Masters
2007/0043269 A1 2/2007 Mannheimer et al.
2007/0073116 A1 3/2007 Kiani et al.
2007/0180140 A1 8/2007 Welch et al.
2007/0244377 A1 10/2007 Cozad et al.
2007/0282478 A1 12/2007 Al-Ali et al.
2008/0064965 A1 3/2008 Jay et al.
2008/0094228 A1 4/2008 Welch et al.
2008/0103375 A1* 5/2008 Kiani .................. A61B 5/0002 600/323
2008/0146892 A1 6/2008 LeBoeuf et al.
2008/0221418 A1 9/2008 Al-Ali et al.
2009/0036759 A1 2/2009 Ault et al.
2009/0043446 A1 2/2009 Drew et al.
2009/0046096 A1* 2/2009 Rampersad ......... G06F 19/3406 345/419
2009/0054743 A1* 2/2009 Stewart .............. A61B 5/02055 600/301
2009/0093687 A1 4/2009 Telfort et al.
2009/0095926 A1 4/2009 MacNeish, III
2009/0171167 A1 7/2009 Baker, Jr.
2009/0182517 A1 7/2009 Gandhi
2009/0184812 A1 7/2009 Drew
2009/0247984 A1 10/2009 Lamego et al.
2009/0259114 A1 10/2009 Johnson et al.
2009/0275813 A1 11/2009 Davis
2009/0275844 A1 11/2009 Al-Ali
2009/0287273 A1* 11/2009 Carlton .................. A61B 34/10 607/45
2010/0004518 A1 1/2010 Vo et al.
2010/0004519 A1 1/2010 Lamego et al.
2010/0030040 A1 2/2010 Poeze et al.
2010/0099964 A1 4/2010 O'Reilly et al.
2010/0234718 A1 9/2010 Sampath et al.
2010/0249549 A1 9/2010 Baker, Jr.
2010/0261979 A1 10/2010 Kiani
2010/0270257 A1 10/2010 Wachman et al.
2011/0001605 A1 1/2011 Kiani et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0087083 A1 4/2011 Poeze et al.
2011/0105854 A1 5/2011 Kiani et al.
2011/0118561 A1 5/2011 Tari et al.
2011/0125060 A1 5/2011 Telfort et al.
2011/0137297 A1 6/2011 Kiani et al.
2011/0172498 A1 7/2011 Olsen et al.
2011/0208015 A1 8/2011 Welch et al.
2011/0213212 A1 9/2011 Al-Ali
2011/0227927 A1 9/2011 Garmon et al.
2011/0230733 A1 9/2011 Al-Ali
2011/0237911 A1 9/2011 Lamego et al.
2011/0237969 A1 9/2011 Eckerbom et al.
2011/0288383 A1 11/2011 Diab
2012/0041316 A1 2/2012 Al-Ali et al.
2012/0046557 A1 2/2012 Kiani
2012/0059267 A1 3/2012 Lamego et al.
2012/0088984 A1 4/2012 Al-Ali et al.
2012/0116175 A1 5/2012 Al-Ali et al.
2012/0123231 A1 5/2012 O'Reilly
2012/0165629 A1 6/2012 Merritt et al.
2012/0179006 A1 7/2012 Jansen et al.
2012/0209082 A1 8/2012 Al-Ali
2012/0209084 A1 8/2012 Olsen et al.
2012/0226117 A1 9/2012 Lamego et al.
2012/0227739 A1 9/2012 Kiani
2012/0283524 A1 11/2012 Kiani et al.
2012/0296178 A1 11/2012 Lamego et al.
2012/0319816 A1 12/2012 Al-Ali
2012/0323086 A1 12/2012 Hansen
2012/0330112 A1 12/2012 Lamego et al.
2013/0023775 A1 1/2013 Lamego et al.
2013/0041591 A1 2/2013 Lamego
2013/0045685 A1 2/2013 Kiani
2013/0046204 A1 2/2013 Lamego et al.
2013/0060147 A1 3/2013 Welch et al.
2013/0096405 A1 4/2013 Garfio
2013/0096936 A1 4/2013 Sampath et al.
2013/0109935 A1 5/2013 Al-Ali et al.
2013/0162433 A1 6/2013 Muhsin et al.
2013/0190581 A1 7/2013 Al-Ali et al.
2013/0197328 A1 8/2013 Diab et al.
2013/0243021 A1 9/2013 Siskavich
2013/0253334 A1 9/2013 Al-Ali et al.
2013/0254717 A1 9/2013 Al-Ali et al.
2013/0262730 A1 10/2013 Al-Ali et al.
2013/0267804 A1 10/2013 Al-Ali
2013/0274571 A1 10/2013 Diab et al.
2013/0274572 A1 10/2013 Al-Ali et al.
2013/0296672 A1 11/2013 O'Neil et al.
2013/0296713 A1 11/2013 Al-Ali et al.
2013/0317370 A1 11/2013 Dalvi et al.
2013/0324808 A1 12/2013 Al-Ali et al.
2013/0331660 A1 12/2013 Al-Ali et al.
2013/0331670 A1 12/2013 Kiani
2013/0338461 A1 12/2013 Lamego et al.
2013/0345921 A1 12/2013 Al-Ali et al.
2014/0012100 A1 1/2014 Al-Ali et al.
2014/0025306 A1 1/2014 Weber et al.
2014/0034353 A1 2/2014 Al-Ali et al.
2014/0051953 A1 2/2014 Lamego et al.
2014/0058230 A1 2/2014 Abdul-Hafiz et al.
2014/0066783 A1 3/2014 Kiani et al.
2014/0077956 A1 3/2014 Sampath et al.
2014/0081100 A1 3/2014 Muhsin et al.
2014/0081175 A1 3/2014 Telfort
2014/0094667 A1 4/2014 Schurman et al.
2014/0100434 A1 4/2014 Diab et al.
2014/0114199 A1 4/2014 Lamego et al.
2014/0120564 A1 5/2014 Workman et al.
2014/0121482 A1 5/2014 Merritt et al.
2014/0121483 A1 5/2014 Kiani
2014/0127137 A1 5/2014 Bellott et al.
2014/0128696 A1 5/2014 Al-Ali
2014/0128699 A1 5/2014 Al-Ali et al.
2014/0129702 A1 5/2014 Lamego et al.
2014/0135588 A1 5/2014 Al-Ali et al.
2014/0142401 A1 5/2014 Al-Ali et al.
2014/0142402 A1 5/2014 Al-Ali et al.
2014/0163344 A1 6/2014 Al-Ali
2014/0163402 A1 6/2014 Lamego et al.
2014/0166076 A1 6/2014 Kiani et al.
2014/0171763 A1 6/2014 Diab
2014/0180038 A1 6/2014 Kiani
2014/0180154 A1 6/2014 Sierra et al.
2014/0180160 A1 6/2014 Brown et al.

(56) References Cited

U.S. PATENT DOCUMENTS

| | | | |
|---|---|---|---|
| 2014/0187973 | A1 | 7/2014 | Brown et al. |
| 2014/0194709 | A1 | 7/2014 | Al-Ali et al. |
| 2014/0194711 | A1 | 7/2014 | Al-Ali |
| 2014/0194766 | A1 | 7/2014 | Al-Ali et al. |
| 2014/0206963 | A1 | 7/2014 | Al-Ali |
| 2014/0213864 | A1 | 7/2014 | Abdul-Hafiz et al. |
| 2014/0243627 | A1 | 8/2014 | Diab et al. |
| 2014/0266790 | A1 | 9/2014 | Al-Ali et al. |
| 2014/0275808 | A1 | 9/2014 | Poeze et al. |
| 2014/0275835 | A1 | 9/2014 | Lamego et al. |
| 2014/0275871 | A1 | 9/2014 | Lamego et al. |
| 2014/0275872 | A1 | 9/2014 | Merritt et al. |
| 2014/0275881 | A1 | 9/2014 | Lamego et al. |
| 2014/0276115 | A1 | 9/2014 | Dalvi et al. |
| 2014/0288400 | A1 | 9/2014 | Diab et al. |
| 2014/0296664 | A1 | 10/2014 | Bruinsma et al. |
| 2014/0303520 | A1 | 10/2014 | Telfort et al. |
| 2014/0309506 | A1 | 10/2014 | Lamego et al. |
| 2014/0316217 | A1 | 10/2014 | Purdon et al. |
| 2014/0316218 | A1 | 10/2014 | Purdon et al. |
| 2014/0316228 | A1 | 10/2014 | Blank et al. |
| 2014/0323825 | A1 | 10/2014 | Al-Ali et al. |
| 2014/0323897 | A1 | 10/2014 | Brown et al. |
| 2014/0323898 | A1 | 10/2014 | Purdon et al. |
| 2014/0330092 | A1 | 11/2014 | Al-Ali et al. |
| 2014/0330098 | A1 | 11/2014 | Merritt et al. |
| 2014/0330099 | A1 | 11/2014 | Al-Ali et al. |
| 2014/0333440 | A1 | 11/2014 | Kiani |
| 2014/0336481 | A1 | 11/2014 | Shakespeare et al. |
| 2014/0343436 | A1 | 11/2014 | Kiani |
| 2014/0357966 | A1 | 12/2014 | Al-Ali et al. |
| 2014/0371548 | A1 | 12/2014 | Al-Ali et al. |
| 2014/0378784 | A1 | 12/2014 | Kiani et al. |
| 2015/0005600 | A1 | 1/2015 | Blank et al. |
| 2015/0011907 | A1 | 1/2015 | Purdon et al. |
| 2015/0012231 | A1 | 1/2015 | Poeze et al. |
| 2015/0018650 | A1 | 1/2015 | Al-Ali et al. |
| 2015/0025406 | A1 | 1/2015 | Al-Ali |
| 2015/0032029 | A1 | 1/2015 | Al-Ali et al. |
| 2015/0038859 | A1 | 2/2015 | Dalvi et al. |
| 2015/0045637 | A1 | 2/2015 | Dalvi |
| 2015/0051462 | A1 | 2/2015 | Olsen |
| 2015/0073241 | A1 | 3/2015 | Lamego |
| 2015/0080754 | A1 | 3/2015 | Purdon et al. |
| 2015/0087936 | A1 | 3/2015 | Al-Ali et al. |
| 2015/0094546 | A1 | 4/2015 | Al-Ali |
| 2015/0097701 | A1 | 4/2015 | Al-Ali et al. |
| 2015/0099950 | A1 | 4/2015 | Al-Ali et al. |
| 2015/0099951 | A1 | 4/2015 | Al-Ali et al. |
| 2015/0099955 | A1 | 4/2015 | Al-Ali et al. |
| 2015/0101844 | A1 | 4/2015 | Al-Ali et al. |
| 2015/0106121 | A1 | 4/2015 | Muhsin et al. |
| 2015/0112151 | A1 | 4/2015 | Muhsin et al. |
| 2015/0116076 | A1 | 4/2015 | Al-Ali et al. |
| 2015/0126830 | A1 | 5/2015 | Schurman et al. |
| 2015/0133755 | A1 | 5/2015 | Smith et al. |
| 2015/0141781 | A1 | 5/2015 | Weber et al. |
| 2015/0165312 | A1 | 6/2015 | Kiani |
| 2015/0196237 | A1 | 7/2015 | Lamego |
| 2015/0196249 | A1 | 7/2015 | Brown et al. |
| 2015/0201874 | A1 | 7/2015 | Diab |
| 2015/0208966 | A1 | 7/2015 | Al-Ali |
| 2015/0216459 | A1 | 8/2015 | Al-Ali et al. |
| 2015/0230755 | A1 | 8/2015 | Al-Ali et al. |
| 2015/0238722 | A1 | 8/2015 | Al-Ali |
| 2015/0245773 | A1 | 9/2015 | Lamego et al. |
| 2015/0245794 | A1 | 9/2015 | Al-Ali |
| 2015/0257689 | A1 | 9/2015 | Al-Ali et al. |
| 2015/0272514 | A1 | 10/2015 | Kiani et al. |
| 2015/0351697 | A1 | 12/2015 | Weber et al. |
| 2015/0351704 | A1 | 12/2015 | Kiani et al. |
| 2015/0359429 | A1 | 12/2015 | Al-Ali et al. |
| 2015/0366472 | A1 | 12/2015 | Kiani |
| 2015/0366507 | A1 | 12/2015 | Blank |
| 2015/0374298 | A1 | 12/2015 | Al-Ali et al. |
| 2015/0380875 | A1 | 12/2015 | Coverston et al. |
| 2016/0000362 | A1 | 1/2016 | Diab et al. |
| 2016/0007930 | A1 | 1/2016 | Weber et al. |
| 2016/0029932 | A1 | 2/2016 | Al-Ali |
| 2016/0029933 | A1 | 2/2016 | Al-Ali et al. |
| 2016/0045118 | A1 | 2/2016 | Kiani |
| 2016/0051205 | A1 | 2/2016 | Al-Ali et al. |
| 2016/0058338 | A1 | 3/2016 | Schurman et al. |
| 2016/0058347 | A1 | 3/2016 | Reichgott et al. |
| 2016/0066823 | A1 | 3/2016 | Kind et al. |
| 2016/0066824 | A1 | 3/2016 | Al-Ali et al. |
| 2016/0066879 | A1 | 3/2016 | Telfort et al. |
| 2016/0072429 | A1 | 3/2016 | Kiani et al. |
| 2016/0081552 | A1 | 3/2016 | Wojtczuk et al. |
| 2016/0095543 | A1 | 4/2016 | Telfort et al. |
| 2016/0095548 | A1 | 4/2016 | Al-Ali et al. |
| 2016/0103598 | A1 | 4/2016 | Al-Ali et al. |
| 2016/0113527 | A1 | 4/2016 | Al-Ali et al. |
| 2016/0143548 | A1 | 5/2016 | Al-Ali |
| 2016/0166182 | A1 | 6/2016 | Al-Ali et al. |
| 2016/0166183 | A1 | 6/2016 | Poeze et al. |
| 2016/0166188 | A1 | 6/2016 | Bruinsma et al. |
| 2016/0166210 | A1 | 6/2016 | Al-Ali |
| 2016/0192869 | A1 | 7/2016 | Kiani et al. |
| 2016/0196388 | A1 | 7/2016 | Lamego |
| 2016/0197436 | A1 | 7/2016 | Barker et al. |
| 2016/0213281 | A1 | 7/2016 | Eckerbom et al. |
| 2016/0228043 | A1 | 8/2016 | O'Neil et al. |
| 2016/0233632 | A1 | 8/2016 | Scruggs et al. |
| 2016/0234944 | A1 | 8/2016 | Schmidt et al. |
| 2016/0270735 | A1 | 9/2016 | Diab et al. |
| 2016/0283665 | A1 | 9/2016 | Sampath et al. |
| 2016/0287090 | A1 | 10/2016 | Al-Ali et al. |
| 2016/0287786 | A1 | 10/2016 | Kiani |
| 2016/0296169 | A1 | 10/2016 | McHale et al. |
| 2016/0310052 | A1 | 10/2016 | Al-Ali et al. |
| 2016/0314260 | A1 | 10/2016 | Kiani |
| 2016/0324486 | A1 | 11/2016 | Al-Ali et al. |
| 2016/0324488 | A1 | 11/2016 | Olsen |
| 2016/0327984 | A1 | 11/2016 | Al-Ali et al. |
| 2016/0328528 | A1 | 11/2016 | Al-Ali et al. |
| 2016/0331332 | A1 | 11/2016 | Al-Ali |
| 2016/0367173 | A1 | 12/2016 | Dalvi et al. |
| 2017/0007134 | A1 | 1/2017 | Al-Ali et al. |
| 2017/0007190 | A1 | 1/2017 | Al-Ali et al. |
| 2017/0007198 | A1 | 1/2017 | Al-Ali et al. |
| 2017/0014083 | A1 | 1/2017 | Diab et al. |
| 2017/0014084 | A1 | 1/2017 | Al-Ali et al. |
| 2017/0021099 | A1 | 1/2017 | Al-Ali et al. |
| 2017/0024748 | A1 | 1/2017 | Haider |
| 2017/0027456 | A1 | 2/2017 | Kinast et al. |
| 2017/0042488 | A1 | 2/2017 | Muhsin |
| 2017/0055851 | A1 | 3/2017 | Ai-Ali |
| 2017/0055882 | A1 | 3/2017 | Al-Ali et al. |
| 2017/0055887 | A1 | 3/2017 | Al-Ali |
| 2017/0055896 | A1 | 3/2017 | Al-Ali et al. |
| 2017/0079594 | A1 | 3/2017 | Telfort et al. |
| 2017/0086723 | A1 | 3/2017 | Al-Ali et al. |
| 2017/0143281 | A1 | 5/2017 | Olsen |
| 2017/0147774 | A1 | 5/2017 | Kiani |
| 2017/0156620 | A1 | 6/2017 | Al-Ali et al. |
| 2017/0173632 | A1 | 6/2017 | Al-Ali |
| 2017/0187146 | A1 | 6/2017 | Kiani et al. |
| 2017/0188919 | A1 | 7/2017 | Al-Ali et al. |
| 2017/0196464 | A1 | 7/2017 | Jansen et al. |
| 2017/0196470 | A1 | 7/2017 | Lamego et al. |
| 2017/0202490 | A1 | 7/2017 | Al-Ali et al. |
| 2017/0224262 | A1 | 8/2017 | Al-Ali |
| 2017/0228516 | A1 | 8/2017 | Sampath et al. |
| 2017/0245790 | A1 | 8/2017 | Al-Ali et al. |
| 2017/0251974 | A1 | 9/2017 | Shreim et al. |
| 2017/0251975 | A1 | 9/2017 | Shreim et al. |
| 2017/0258403 | A1 | 9/2017 | Abdul-Hafiz et al. |
| 2017/0311851 | A1 | 11/2017 | Schurman et al. |
| 2017/0311891 | A1 | 11/2017 | Kiani et al. |
| 2017/0325728 | A1 | 11/2017 | Al-Ali et al. |
| 2017/0332976 | A1 | 11/2017 | Al-Ali et al. |
| 2017/0340293 | A1 | 11/2017 | Al-Ali et al. |
| 2017/0360310 | A1 | 12/2017 | Kiani et al. |

(56) References Cited

U.S. PATENT DOCUMENTS

| | | | |
|---|---|---|---|
| 2017/0367632 | A1 | 12/2017 | Al-Ali et al. |
| 2018/0008146 | A1 | 1/2018 | Al-Ali et al. |
| 2018/0013562 | A1 | 1/2018 | Haider et al. |
| 2018/0014752 | A1 | 1/2018 | Al-Ali et al. |
| 2018/0028124 | A1 | 2/2018 | Al-Ali et al. |
| 2018/0055385 | A1 | 3/2018 | Al-Ali |
| 2018/0055390 | A1 | 3/2018 | Kiani et al. |
| 2018/0055430 | A1 | 3/2018 | Diab et al. |
| 2018/0064381 | A1 | 3/2018 | Shakespeare et al. |
| 2018/0069776 | A1 | 3/2018 | Lamego et al. |
| 2018/0070867 | A1 | 3/2018 | Smith et al. |
| 2018/0082767 | A1 | 3/2018 | Al-Ali et al. |
| 2018/0085068 | A1 | 3/2018 | Telfort |
| 2018/0087937 | A1 | 3/2018 | Al-Ali et al. |
| 2018/0103874 | A1 | 4/2018 | Lee et al. |
| 2018/0103905 | A1 | 4/2018 | Kiani |
| 2018/0110478 | A1 | 4/2018 | Ai-Ali |
| 2018/0116575 | A1 | 5/2018 | Perea et al. |
| 2018/0125368 | A1 | 5/2018 | Lamego et al. |
| 2018/0125430 | A1 | 5/2018 | Al-Ali et al. |
| 2018/0125445 | A1 | 5/2018 | Telfort et al. |
| 2018/0130325 | A1 | 5/2018 | Kiani et al. |
| 2018/0132769 | A1 | 5/2018 | Weber et al. |
| 2018/0132770 | A1 | 5/2018 | Lamego |
| 2018/0146901 | A1 | 5/2018 | Al-Ali et al. |
| 2018/0146902 | A1 | 5/2018 | Kiani et al. |
| 2018/0153442 | A1 | 6/2018 | Eckerbom et al. |
| 2018/0153446 | A1 | 6/2018 | Kiani |
| 2018/0153447 | A1 | 6/2018 | Al-Ali et al. |
| 2018/0153448 | A1 | 6/2018 | Weber et al. |
| 2018/0161499 | A1 | 6/2018 | Al-Ali et al. |
| 2018/0168491 | A1 | 6/2018 | Al-Ali et al. |
| 2018/0174679 | A1 | 6/2018 | Sampath et al. |
| 2018/0174680 | A1 | 6/2018 | Sampath et al. |
| 2018/0182484 | A1 | 6/2018 | Sampath et al. |
| 2018/0184917 | A1 | 7/2018 | Kiani |
| 2018/0192924 | A1 | 7/2018 | Al-Ali |
| 2018/0192953 | A1 | 7/2018 | Shreim et al. |
| 2018/0192955 | A1 | 7/2018 | Al-Ali et al. |
| 2018/0199871 | A1 | 7/2018 | Pauley et al. |
| 2018/0206795 | A1 | 7/2018 | Ai-Ali |
| 2018/0206815 | A1 | 7/2018 | Telfort |
| 2018/0213583 | A1 | 7/2018 | Al-Ali |
| 2018/0214031 | A1 | 8/2018 | Kiani et al. |
| 2018/0214090 | A1 | 8/2018 | Al-Ali et al. |
| 2018/0216370 | A1 | 8/2018 | Ishiguro et al. |
| 2018/0218792 | A1 | 8/2018 | Muhsin et al. |
| 2018/0225960 | A1 | 8/2018 | Al-Ali et al. |
| 2018/0238718 | A1 | 8/2018 | Dalvi |
| 2018/0242853 | A1 | 8/2018 | Al-Ali |
| 2018/0242921 | A1 | 8/2018 | Muhsin et al. |
| 2018/0242923 | A1 | 8/2018 | Al-Ali et al. |
| 2018/0242924 | A1 | 8/2018 | Barker et al. |
| 2018/0242926 | A1 | 8/2018 | Muhsin et al. |
| 2018/0247353 | A1 | 8/2018 | Al-Ali et al. |
| 2018/0247712 | A1 | 8/2018 | Muhsin et al. |
| 2018/0249933 | A1 | 9/2018 | Schurman et al. |
| 2018/0253947 | A1 | 9/2018 | Muhsin et al. |
| 2018/0256087 | A1 | 9/2018 | Al-Ali et al. |
| 2018/0256113 | A1 | 9/2018 | Weber et al. |
| 2018/0285094 | A1 | 10/2018 | Housel et al. |
| 2018/0289325 | A1 | 10/2018 | Poeze et al. |
| 2018/0289337 | A1 | 10/2018 | Al-Ali et al. |
| 2018/0296161 | A1 | 10/2018 | Shreim et al. |
| 2018/0300919 | A1 | 10/2018 | Muhsin et al. |
| 2018/0310822 | A1 | 11/2018 | Indorf et al. |
| 2018/0310823 | A1 | 11/2018 | Al-Ali et al. |
| 2018/0317826 | A1 | 11/2018 | Muhsin |
| 2018/0317841 | A1 | 11/2018 | Novak, Jr. |
| 2018/0333055 | A1 | 11/2018 | Lamego et al. |
| 2018/0333087 | A1 | 11/2018 | Al-Ali |
| 2019/0000317 | A1 | 1/2019 | Muhsin et al. |
| 2019/0000362 | A1 | 1/2019 | Kiani et al. |
| 2019/0015023 | A1 | 1/2019 | Monfre |
| 2019/0021638 | A1 | 1/2019 | Al-Ali et al. |
| 2019/0029574 | A1 | 1/2019 | Schurman et al. |
| 2019/0029578 | A1 | 1/2019 | Al-Ali et al. |
| 2019/0058280 | A1 | 2/2019 | Al-Ali et al. |
| 2019/0058281 | A1 | 2/2019 | Al-Ali et al. |
| 2019/0069813 | A1 | 3/2019 | Al-Ali |
| 2019/0069814 | A1 | 3/2019 | Al-Ali |
| 2019/0076028 | A1 | 3/2019 | Al-Ali et al. |
| 2019/0082979 | A1 | 3/2019 | Al-Ali et al. |
| 2019/0090748 | A1 | 3/2019 | Al-Ali |
| 2019/0090760 | A1 | 3/2019 | Kinast et al. |
| 2019/0090764 | A1 | 3/2019 | Al-Ali |
| 2019/0117070 | A1 | 4/2019 | Muhsin et al. |
| 2019/0117139 | A1 | 4/2019 | Al-Ali et al. |
| 2019/0117140 | A1 | 4/2019 | Al-Ali et al. |
| 2019/0117141 | A1 | 4/2019 | Al-Ali |
| 2019/0117930 | A1 | 4/2019 | Al-Ali |
| 2019/0122763 | A1 | 4/2019 | Sampath et al. |
| 2019/0133525 | A1 | 5/2019 | Al-Ali et al. |
| 2019/0142283 | A1 | 5/2019 | Lamego et al. |
| 2019/0142344 | A1 | 5/2019 | Telfort et al. |
| 2019/0150856 | A1 | 5/2019 | Kiani et al. |
| 2019/0167161 | A1 | 6/2019 | Al-Ali et al. |
| 2019/0175019 | A1 | 6/2019 | Al-Ali et al. |
| 2019/0192076 | A1 | 6/2019 | McHale et al. |
| 2019/0200941 | A1 | 7/2019 | Chandran et al. |
| 2019/0201623 | A1 | 7/2019 | Kiani |
| 2019/0209025 | A1 | 7/2019 | Al-Ali |
| 2019/0214778 | A1 | 7/2019 | Scruggs et al. |
| 2019/0216319 | A1 | 7/2019 | Poeze et al. |
| 2019/0216379 | A1 | 7/2019 | Al-Ali et al. |
| 2019/0221966 | A1 | 7/2019 | Kiani et al. |
| 2019/0223804 | A1 | 7/2019 | Blank et al. |
| 2019/0231199 | A1 | 8/2019 | Al-Ali et al. |
| 2019/0231241 | A1 | 8/2019 | Al-Ali et al. |
| 2019/0231270 | A1 | 8/2019 | Abdul-Hafiz et al. |
| 2019/0239787 | A1 | 8/2019 | Pauley et al. |
| 2019/0239824 | A1 | 8/2019 | Muhsin et al. |
| 2019/0254578 | A1 | 8/2019 | Lamego |
| 2019/0261857 | A1 | 8/2019 | Al-Ali |
| 2019/0269370 | A1 | 9/2019 | Al-Ali et al. |
| 2019/0274606 | A1 | 9/2019 | Kiani et al. |
| 2019/0274627 | A1 | 9/2019 | Al-Ali et al. |
| 2019/0274635 | A1 | 9/2019 | Al-Ali et al. |
| 2019/0290136 | A1 | 9/2019 | Dalvi et al. |
| 2019/0298270 | A1 | 10/2019 | Al-Ali et al. |
| 2019/0304601 | A1 | 10/2019 | Sampath et al. |
| 2019/0304605 | A1 | 10/2019 | Al-Ali |
| 2019/0320906 | A1 | 10/2019 | Olsen |
| 2019/0374139 | A1 | 12/2019 | Kiani et al. |
| 2019/0374173 | A1 | 12/2019 | Kiani et al. |
| 2019/0374713 | A1 | 12/2019 | Kiani et al. |
| 2020/0021930 | A1 | 1/2020 | Iswanto et al. |
| 2020/0060869 | A1 | 2/2020 | Telfort et al. |
| 2020/0111552 | A1 | 4/2020 | Ahmed |
| 2020/0113435 | A1 | 4/2020 | Muhsin |
| 2020/0113488 | A1 | 4/2020 | Al-Ali et al. |
| 2020/0113496 | A1 | 4/2020 | Scruggs et al. |
| 2020/0113497 | A1 | 4/2020 | Triman et al. |
| 2020/0113520 | A1 | 4/2020 | Abdul-Hafiz et al. |
| 2020/0138288 | A1 | 5/2020 | Al-Ali et al. |
| 2020/0138368 | A1 | 5/2020 | Kiani et al. |
| 2020/0163597 | A1 | 5/2020 | Dalvi et al. |
| 2020/0196877 | A1 | 6/2020 | Vo et al. |
| 2020/0253474 | A1 | 8/2020 | Muhsin et al. |
| 2020/0253544 | A1 | 8/2020 | Belur Nagaraj et al. |
| 2020/0275841 | A1 | 9/2020 | Telfort et al. |
| 2020/0288983 | A1 | 9/2020 | Telfort et al. |
| 2020/0321793 | A1 | 10/2020 | Al-Ali et al. |
| 2020/0329983 | A1 | 10/2020 | Al-Ali et al. |
| 2020/0329984 | A1 | 10/2020 | Al-Ali et al. |
| 2020/0329993 | A1 | 10/2020 | Al-Ali et al. |
| 2020/0330037 | A1 | 10/2020 | Al-Ali et al. |
| 2021/0022628 | A1 | 1/2021 | Telfort et al. |
| 2021/0104173 | A1 | 4/2021 | Pauley et al. |
| 2021/0113121 | A1 | 4/2021 | Diab et al. |
| 2021/0117525 | A1 | 4/2021 | Kiani et al. |
| 2021/0118581 | A1 | 4/2021 | Kiani et al. |
| 2021/0121582 | A1 | 4/2021 | Krishnamani et al. |
| 2021/0161465 | A1 | 6/2021 | Barker et al. |

(56) References Cited

U.S. PATENT DOCUMENTS

| | | | |
|---|---|---|---|
| 2021/0236729 | A1 | 8/2021 | Kiani et al. |
| 2021/0256267 | A1 | 8/2021 | Ranasinghe et al. |
| 2021/0256835 | A1 | 8/2021 | Ranasinghe et al. |
| 2021/0275101 | A1 | 9/2021 | Vo et al. |
| 2021/0290060 | A1 | 9/2021 | Ahmed |
| 2021/0290072 | A1 | 9/2021 | Forrest |
| 2021/0290080 | A1 | 9/2021 | Ahmed |
| 2021/0290120 | A1 | 9/2021 | Al-Ali |
| 2021/0290177 | A1 | 9/2021 | Novak, Jr. |
| 2021/0290184 | A1 | 9/2021 | Ahmed |
| 2021/0296008 | A1 | 9/2021 | Novak, Jr. |
| 2021/0330228 | A1 | 10/2021 | Olsen et al. |
| 2021/0386382 | A1 | 12/2021 | Olsen et al. |
| 2021/0402110 | A1 | 12/2021 | Pauley et al. |
| 2022/0026355 | A1 | 1/2022 | Normand et al. |
| 2022/0039707 | A1 | 2/2022 | Sharma et al. |
| 2022/0053892 | A1 | 2/2022 | Al-Ali et al. |
| 2022/0071562 | A1 | 3/2022 | Kiani |
| 2022/0096603 | A1 | 3/2022 | Kiani et al. |
| 2022/0151521 | A1 | 5/2022 | Krishnamani et al. |
| 2022/0218244 | A1 | 7/2022 | Kiani et al. |
| 2022/0287574 | A1 | 9/2022 | Telfort et al. |
| 2022/0296161 | A1 | 9/2022 | Al-Ali et al. |
| 2022/0361819 | A1 | 11/2022 | Al-Ali et al. |
| 2022/0379059 | A1 | 12/2022 | Yu et al. |
| 2022/0392610 | A1 | 12/2022 | Kiani et al. |
| 2023/0028745 | A1 | 1/2023 | Al-Ali |
| 2023/0038389 | A1 | 2/2023 | Vo |
| 2023/0045647 | A1 | 2/2023 | Vo |
| 2023/0058052 | A1 | 2/2023 | Al-Ali |
| 2023/0058342 | A1 | 2/2023 | Kiani |
| 2023/0069789 | A1 | 3/2023 | Koo et al. |
| 2023/0087671 | A1 | 3/2023 | Telfort et al. |
| 2023/0110152 | A1 | 4/2023 | Forrest et al. |
| 2023/0111198 | A1 | 4/2023 | Yu et al. |
| 2023/0115397 | A1 | 4/2023 | Vo et al. |
| 2023/0116371 | A1 | 4/2023 | Mills et al. |
| 2023/0135297 | A1 | 5/2023 | Kiani et al. |
| 2023/0138098 | A1 | 5/2023 | Telfort et al. |
| 2023/0145155 | A1 | 5/2023 | Krishnamani et al. |
| 2023/0147750 | A1 | 5/2023 | Barker et al. |
| 2023/0210417 | A1 | 7/2023 | Al-Ali et al. |
| 2023/0222805 | A1 | 7/2023 | Muhsin et al. |
| 2023/0222887 | A1 | 7/2023 | Muhsin et al. |
| 2023/0226331 | A1 | 7/2023 | Kiani et al. |
| 2023/0284916 | A1 | 9/2023 | Telfort |
| 2023/0284943 | A1 | 9/2023 | Scruggs et al. |
| 2023/0301562 | A1 | 9/2023 | Scruggs et al. |
| 2023/0346993 | A1 | 11/2023 | Kiani et al. |
| 2023/0368221 | A1 | 11/2023 | Haider |
| 2023/0371893 | A1 | 11/2023 | Al-Ali et al. |
| 2023/0389837 | A1 | 12/2023 | Krishnamani et al. |
| 2024/0016418 | A1 | 1/2024 | Devadoss et al. |
| 2024/0016419 | A1 | 1/2024 | Devadoss et al. |
| 2024/0047061 | A1 | 2/2024 | Al-Ali et al. |
| 2024/0049310 | A1 | 2/2024 | Al-Ali et al. |
| 2024/0049986 | A1 | 2/2024 | Al-Ali et al. |
| 2024/0081656 | A1 | 3/2024 | DeJong et al. |
| 2024/0122486 | A1 | 4/2024 | Kiani |
| 2024/0180456 | A1 | 6/2024 | Al-Ali |
| 2024/0188872 | A1 | 6/2024 | Al-Ali et al. |
| 2024/0245855 | A1 | 7/2024 | Vo et al. |
| 2024/0260894 | A1 | 8/2024 | Olsen |
| 2024/0267698 | A1 | 8/2024 | Telfort et al. |
| 2024/0277233 | A1 | 8/2024 | Ai-Ali |
| 2024/0277280 | A1 | 8/2024 | Al-Ali |
| 2024/0298920 | A1 | 9/2024 | Fernkbist et al. |
| 2024/0306985 | A1 | 9/2024 | Vo et al. |
| 2024/0324953 | A1 | 10/2024 | Telfort |
| 2024/0380246 | A1 | 11/2024 | Moran |
| 2024/0380247 | A1 | 11/2024 | Moran |
| 2024/0404549 | A1 | 12/2024 | Campbell et al. |
| 2025/0000458 | A1 | 1/2025 | Abdul-Hafiz et al. |
| 2025/0037836 | A1 | 1/2025 | Kiani |
| 2025/0100482 | A1 | 3/2025 | Al-Ali et al. |
| 2025/0118415 | A1 | 4/2025 | Olsen |
| 2025/0255764 | A1 | 8/2025 | Stead |
| 2025/0278512 | A1 | 9/2025 | Koo et al. |
| 2025/0281059 | A1 | 9/2025 | Avendano |
| 2025/0288250 | A1 | 9/2025 | Al-Ali et al. |
| 2025/0295366 | A1 | 9/2025 | Al-Ali et al. |
| 2025/0302426 | A1 | 10/2025 | Ha et al. |
| 2025/0311949 | A1 | 10/2025 | Al-Ali et al. |
| 2025/0318761 | A1 | 10/2025 | Al-Ali et al. |
| 2025/0322950 | A1 | 10/2025 | Al-Ali et al. |
| 2025/0323417 | A1 | 10/2025 | Rey |
| 2025/0329240 | A1 | 10/2025 | Kiani |
| 2025/0344010 | A1 | 11/2025 | Al-Ali et al. |
| 2026/0014333 | A1 | 1/2026 | Fernkvist et al. |
| 2026/0014334 | A1 | 1/2026 | Danwihl |
| 2026/0048198 | A1 | 2/2026 | Vo et al. |

OTHER PUBLICATIONS

U.S. Appl. No. 10/325,681, filed Jun. 18, 2019, Sampath et al.

U.S. Appl. No. 10/327,337, filed Jun. 18, 2019, Triman et al.

U.S. Appl. No. 10/420,493, filed Sep. 24, 2019, Al-Ali et al.

BMI Scale, "How to Translate BMI into Pounds: Finally, a Body Mass Index Calculator for the Rest of Us", http://web.archive.org/web/20080620122802/http://www.prweb.com/releases/2005/07/prweb262133.htm, archived on Jun. 20, 2008.

Excel Univariate, http://web.archive.org/web/20090228103558/http://cameron.econ.ucdavis.edu/excel/ex11histogram.html, archived on Feb. 29, 2009.

MVP-50P Instrument Marking Requirements for Certified Aircraft, http://web.archive.org/web/20090306210759/http://www.buy-ei.com/Information/Redlines_Limits_MVP.pdf, archived on Mar. 6, 2009.

MVP-50P Overview, http://web.archive.org/web/20090422043625/http://www.buy-ei.com/Pages/MVP/MVP-50P_Overview.html, archived Apr. 22, 2009.

* cited by examiner

CONFIGURABLE PATIENT MONITORING SYSTEM

INCORPORATION BY REFERENCE TO ANY PRIORITY APPLICATIONS

Any and all applications for which a foreign or domestic priority claim is identified in the Application Data Sheet as filed with the present application are incorporated by reference under 37 CFR 1.57 and made a part of this specification.

BACKGROUND

Field of the Invention

The present disclosure relates to the field of patient monitoring systems.

Description of the Related Art

Patient monitoring systems are used to track and monitor the health and wellness of a patient. A patient's health can be monitored using physiological sensors to record and process a patient's vital signs, such as, pulse rate, temperature, glucose level, and other physiological parameters. A medical practitioner can use this information to track the health of a patient. Each patient has different physiological characteristics, such as gender, age, weight, height, fitness, medical history, and other characteristics, which can affect the range of signals that are considered healthy for each person. For example, the normal resting heart rate for an athlete may be close to fifty beats per minute, whereas for another adult, the normal resting heart rate may be closer to one hundred beats per minute. As such it can be difficult for medical practitioners to quickly evaluate the health of the patient without consulting additional information prior to analyzing the patient's physiological signals, which can be a time consuming process. In some cases, a patient's physiological signals may appear healthy, even though the patient is in need of medical attention. Additional, typical sensors only display the current value for a patient's physiological sensors, which can make it difficult for a medical practitioner to identify trends in the patient's health.

SUMMARY

Patient monitoring systems can help health practitioners to quickly evaluate a patient's state of health and wellness by providing health indicators that help differentiate between healthy and unhealthy signals. Indicators that are easy to see and understand quickly are critical in the patient care industry. Even more important are indicators that can be readily understood by less educated care providers and by those that speak and/or read a different language than the device displays. In some embodiments of this disclosure, customized health indicators can be configured to account for a patient's specific physiological parameters, including medical history, current medications, and other health considerations. These customizations can assist in the quick recognition of potential problems by the less educated and foreign language observers. In some embodiments, the health indicators can be configured to show the signal over a period of time, which can help a medical practitioner identify how the patient's health is trending.

In one embodiment, a patient monitoring system has a first physiological sensor that is configured to measure at least one physiological signal from a patient. A health indicator is configured to display a signal value based on the output of at least one physiological signal. The patient monitoring system is configured to receive patient information and calculate a first range of values and a second range of values for the health indicator. The first range of values corresponds to a first range of physiological signals from the patient and to a healthy patient condition. The second range of values corresponds to a second range of physiological signals from the patient and to an unhealthy patient condition. In some embodiments the calculated ranges can be based at least in part on patient information. The patient monitoring system also has a user interface configured to display the health indicator. The health indicator is configured to display a first output when the signal value is within the first range of values and the health indicator is configured to display a second output when the signal value is within the second range of values.

In some embodiments the patient monitoring system is further configured to calculate a third range of values for the health indicator. The third range of values corresponds to a third range of physiological signals from the patient and corresponds to an intermediate patient condition. In some embodiments, the first, second, and the third ranges of values can overlap.

In some embodiments the health indicator is configured to output an alarm signal when the signal value moves from the first range of values to the second range of values. The alarm signal can be an audible alarm, an electronic message, a visual alarm, or other type of alert system. The patient monitoring system can be configured to communicate with remote devices.

In some embodiments, the first output can be a first color displayed on the health indicator. The second output can be a second color displayed on the health indicator. The first output and the second output can both be displayed when the signal value is in the second range of values.

In some embodiments, the patient information can be age, gender, medical history, or other information about the patient. The health indicator can be number of different indicators such as, a circular indicator, a vertical bar indicator, a trend graph indicator, a Gaussian trend indicator, combinations of the one or more indicators, or other types of indicator. The signal value can be a point on a trend graph, a numeric value, an analog indicator, or other type of representation of the physiological signal value. The physiological sensor can be configured to measure glucose, blood pressure, pulse rate, respiration rate, oxygen saturation, total hemoglobin, carboxyhemoglobin, methemoglobin, perfusion index, temperature, or other physiological parameter. The physiological sensor can be a pulse oximeter, a heart rate monitor, respiratory monitor (e.g., an acoustic monitor), a thermometer, or other physiological sensor.

An embodiment of a method of monitoring a patient has the steps of measuring at least one physiological signal from a patient using a physiological sensor, providing a first health indicator having a signal value based upon the at least one physiological signal, receiving patient information, and calculating a first range of values for the health indicator. The first range of values corresponds to a first range of physiological signals from the patient and to a first patient condition. The method also includes calculating a second range of values for the health indicator. The second range of values corresponds to a second range of physiological signals from the patient and to a second patient condition. The method also includes displaying the first health indicator on a user interface. The first range of values and the second range of values are displayed on the first health indicator. The method also includes displaying the signal value on the first health indicator, displaying a first output on the health indicator when the first value is within the first range of values, and displaying a second output on the health indicator when the second value is within the second range of values.

In some embodiments the method includes the step of displaying a threshold indicator separating the first range of values from the second range of values.

DETAILED DESCRIPTION

Figure 5:
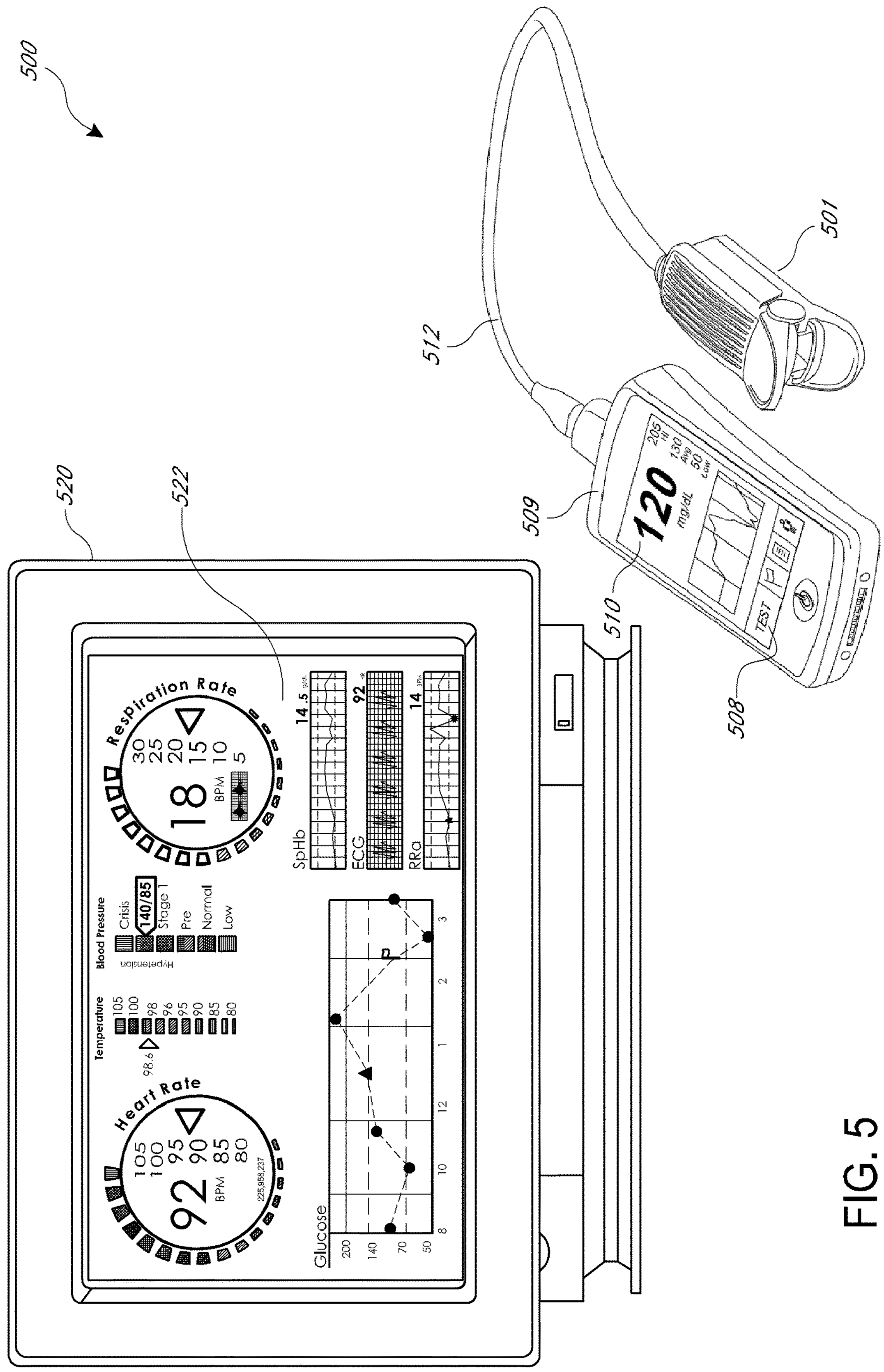
FIG. 5 illustrates an embodiment of an exemplary handheld monitor having a display and an exemplary noninvasive optical sensor of a patient monitoring system.

A patient monitoring system can display one or more of a patient's physiological parameters using one or more configurable health indicators on a configurable user interface. Each health indicators can display one or more physiological parameters of the patient. The health indicators can be configured to be easy to read and interpret. The health indicators can include one or more thresholds that can help medical practitioners to evaluate the health and wellness of a patient. The patient monitoring system can display health indicators for a patient's physiological parameters, including heart rate, respiration rate, oxygen saturation (Sp02, % Sp02), temperature, blood pressure, total hemoglobin (SpHb), perfusion index (PI), carboxyhemoglobin (SpCO), methemoglobin, and other physiological parameters. The physiological signals displayed in each health indicator can be represented by one or more analog indicators and/or one or more digital indicators. The health indicators can be a variety of types including a trend graphs, Gaussian trend graphs, circle indicators, arc indicators, bar indicators, line indicators, and/or other types of indicators. In some embodiments, a health indicator can combine one or more physiological parameters as part of a single health indicator. The displayed values for the health indicators can be derived from sensor signals taken from a patient. For example, pulse rate, blood pressure, and respiration rate can be normalized and combined to determine an overall health indicator. Physiological sensors capable of reading physiological signals are available from healthcare products manufacturers, such as Masimo Corporation located of Irvine, California. An example of a physiological sensor and patient monitor is illustrated in FIG. 5.

A user interface of the patient monitoring system can be configured to display the health indicators. The user interfaces can be customized for each patient. The user interface of the patient monitoring system can provide a centralized display of a patient's health and wellness information. In some embodiments, the patient monitoring system can be configured to display all of and the information associated with the patient on a single display console. In some embodiments the user interface can be displayed on a plurality of display consoles. Each screen of the user interface can be configured to display one or more health indicators and other information associated with the patient. In some embodiments the health indicators can be configured to be displayed on a handheld display or handheld patient monitor.

The user interface is configurable and can be configured individually for each patient. A user can configure the user interface. In some embodiments the patient monitoring system can configure the user interface. In some embodiments, the user interface can be generated automatically based on the physiological sensors connected to the patient monitoring system. In some embodiments, the user interface can be configured using a template and/or preconfigured health indicators. Preconfigured user interfaces and health indicators can be further configured and adjusted by the user. The health indicators may include both analog and digital indicators. The analog and digital indicators can be positioned in any number of formations, such as side-by-side, above, below, transposed, etc. The number, type, and arrangement of the health indicators displayed can be determined by various factors, including, the number of physiological sensors, the type of physiological sensors, the settings of the user interface, the hardware configuration, the software configuration, and other factors. Embodiments of user interfaces are illustrated in FIGS. 1 through 4.

Analog and digital indicators can display measurements of physiological parameters. The indicators can indicate an actual level or a normalized level. The user interfaces can also display information, such as network connection status, network connection strength, network type, power levels, battery power, time, patient identifying information, health provider information, sensor signal confidence levels, sensor placement, and other information.

In some embodiments a user interface can be configured to display health indicators for each physiological sensor connected to a patient. In some embodiments, a plurality of user interface screens can be configured to display a patient's health information. The user interface screens can be displayed on one or more display consoles. The patient monitoring system can be configured to transfer the signal information to a remote source over a network. In some embodiments the user interface information can be displayed and formatted for viewing on portable computing device, such as a laptop computer, a mobile phone, a tablet computer, and/or other computing device.

Figure 1:
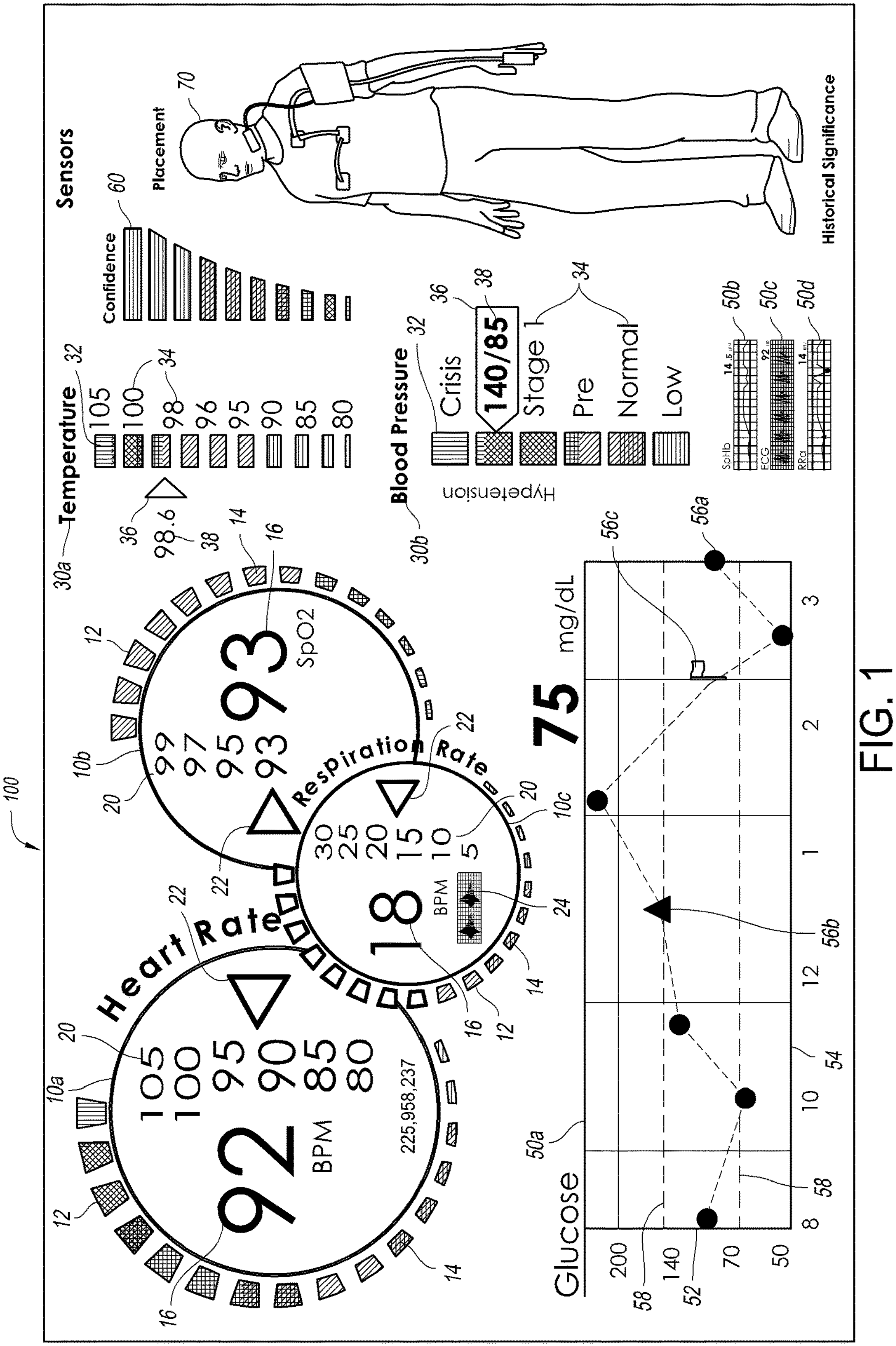
FIG. 1 is an embodiment of a user interface showing a plurality of health indicators.

FIGS. 1 through 4 illustrate embodiments of configurable user interfaces. FIG. 1 is an embodiment of user interface 100 displaying a plurality of analog and digital health indicators. The user interface 100 includes health indicators for heart rate 10*a*, respiration rate 10*b*, oxygen saturation (SpO2) 10*c*, temperature 30*a*, blood pressure 30*b*, glucose 50*a*, total hemoglobin (SpHb) 50*b*, ECG 50*c*, and respiration rate (RRa) 50*d*. The user interface 100 also includes sensor confidence 60, and sensor placement 70 indicators.

The user interface 100 has three circular health indicators for heart rate 10*a*, respiration rate 10*b* and oxygen saturation (SpO2) 10*c*. The circular health indicators have shaped blocks 12 arranged circumferentially around the circular indicator. The blocks 12 increase in size from smaller to larger about the circle. The blocks 12 can illuminate as the value of the measured physiological parameter increases. In some embodiments the blocks display a muted color for each block 12 when the block 12 is not illuminated, such as in indicators 10*a* and 10*c*. In some embodiments, the blocks 12 can be clear or display a background color when not illuminated, as in 10*b*. In some embodiments an arrow or other measurement indicator can point to a specific value on the indicator.

A color pattern 14 can be associated with the blocks 12. The color pattern 14 can be configured to indicate patient wellness. The colors of the blocks 12 can help medical practitioners to quickly and easily determine the current status of the physiological parameter. In one embodiment, green can indicate a healthy or normal condition, yellow can indicate deteriorating conditions, and red can indicate critical or severe conditions. In some embodiments, other colors can be used to indicate patient wellness. In some embodiments the blocks 12 can gradually change color around the entire circle moving through blue, green, yellow, orange and, and red, where each block 12 can have one or more colors, as illustrated by patterns 14 on the heart rate indicator 10*a*. In some embodiment each block 12 can have a discrete color, as illustrated by the color patterns 14 on indicator 10*c*. In some embodiments, red can be used to indicate that a value is too high or too low. In some embodiments, other colors can be used to indicate when the measurements are too low or too high.

In some embodiments, a numeric indicator 16 can be displayed within the circular indicator 10*a-c*. A measurement unit, such as BPM, can be associated with the numeric indicator. The numeric value 16 indicates the current measurement of the physiological sensor. In some embodiments the numeric value 16 can be colored to match the color of the associated blocks 12. In some embodiments the numeric value can be colored to match a color typically associated with the physiological parameter. In some embodiments, the circular indicators 10*a-c* can include time based data 24, such as a respiration auditory waveform or a plethysmograph. The time based data 24 can display the measured signal over a period of time and/or a specific number of measurements.

In some embodiments, the circular indicators 10*a-c* can include dial indicators 20. The numbers of the dial 20 can move past a stationary pointer 22, such as an arrow. The pointer 22 indicates the current measurement of the physiological sensors, similar to numeric value 16. The dial 20 can scroll up and down to indicate the current value. In some embodiments the pointer 22 can move up and down to indicate the current measurement. In some embodiments the numbers of the dial 20 and/or the arrow 22 may be colored to indicate the level of patient wellness, similar to blocks 12.

The user interface 100 has vertical bar indicators, temperature 30*a* and blood pressure 30*b*. The bar indicators 30*a-b* have a plurality of bars 32, descriptors 34, a measurement indicator 36, and a measured value 38. The bars 32 can have a color pattern 14. In some embodiments, the bars 32 can be implemented as dots, dashes, arrow, rectangles, squares, or the like. The indicators 30*a-b* can have descriptors 34, such as numbers, words, or symbols relating to the measured condition. The measurement pointer 36 can move up and down along the vertical scale to indicate the current measurement of the physiological sensors. In some embodiments, the bars can scroll through the values and the pointer 36 can remain stationary. The pointer 36 can be implemented using other shapes such as an arrow, circle, star, line or other shape. A measured value 38 can be associated with the pointer 36. The indicator 36 and/or the measured value 38 can be colored to indicate the level of patient wellness. In some embodiments the bars and/or descriptors can illuminate or flash based on the occurrence of an event, such as an alarm.

The temperature indicator 30*a*, in this embodiment, has numeric descriptors 34 with an arrow-shaped pointer 36. The pointer 36 moves up and down the bars 32 to indicate the current temperature value. The measured value 38 shows a numeric value for the current measurement of the patient's temperature.

The blood pressure indicator 30*b*, in this embodiment, has a plurality of bars 32, with each bar 32 associated with a text descriptor 34. The descriptors 34 indicate conditions relating to blood pressure measurements, including stages of hypertension. The pointer 36 is a block arrow with a value 38 showing the current blood pressure measurement. Each bar 32 has an associated range of measurement values. The pointer 36 moves discretely between bars. The pointer 36 only moves between bars 32 when an upper or lower threshold has been surpassed.

The user interface 100 also includes sensor information, such as sensor confidence indicators 60 and sensor placement indicators 70. The sensor confidence indicator 60 can display the strength and integrity of the sensor signal. In this embodiment the sensor confidence indicator is a vertical bar chart with bars illustrating the relative strength of the sensor signals. In some embodiments the indicator can be color coded. In some embodiments there can be a sensor confidence indicator for each sensor. Sensor confidence indicators can be used to provide information for any of the sensors used by the patient monitoring system.

The sensor placement indicator 70 shows the relative placement of each sensor on the patient. The sensor placement indicator shows an illustration of the patient with the positioning of each sensors connected to the patient. The illustration can change to match the characteristics of the actual patient (e.g., man, woman, child, elderly, etc.). The indicator can display the recommended or expected placement of the sensor on the patient. In some embodiments, the sensor placement indicator can show the actual position of the sensor(s) on the patient.

The user interface 100 also includes trend graphs to show physiological parameter measurements over time, such as glucose 50*a*, total hemoglobin (SpHb) 50*b*, ECG, 50*c*, and respiration rate (RRa) 50*d*. The trend indicators can help to identify trends in a patient's health, such as when a patient is moving from a healthy condition toward an unhealthy condition. Trends in the patient's measurements can be shown by displaying physiological measurements over a period of time. Trend graph 50*a* includes a vertical axis 52, a horizontal axis 54, a measurement indicator 56, and threshold levels 58. The trend graph 50*a* shows measurements of the physiological parameters over a defined time period. The vertical axis 52 indicates the magnitude of the measurement and the horizontal axis 54 indicates time. In some embodiments the vertical and horizontal axes may not have values displayed. In some embodiments, the current value of the physiological parameter can be displayed on the upper right side of the trend graph.

The measurements can show discrete measurements with continuous measurements in real-time. In some embodiments, the measurement indicator 56 can be used to provide additional information about the measurement data. For example, a circle indicator 56*a* can indicate discrete non-invasive measurements and a triangle indicator 56*b* can indicate a discrete invasive measurement. Other shapes, such as a flag indicator 56*c*, can be used to show other conditions and/or measurements. In some embodiments, an indicator 56 can be used to show when a measurement has exceeded an upper or lower threshold. The type of measurement indicator 56 can be used to indicate a severe or critical condition based on multiple measurements from different physiological parameters. For discrete measurements, connecting lines, such as a dashed line, may be added between measurements to better visualize the trends of the measurements. For real-time or continuous measurements the information can be shown as a solid line. In some embodiments, the most recent or current value may be displayed above the graph. Threshold levels 58 may be shown on the trend graph. The threshold levels 58 can indicate upper and/or lower thresholds, such as in 50*a*, 50*b*, and 50*d*. The threshold levels 58 may be accompanied by threshold descriptors, as illustrated by the trend graph 150 in FIG. 3. Trend graphs 50*b-d* have the same characteristics as those described in association with trend graph 50*a*.

The trend graph 50*a-d* may be scaled and shaped as appropriate to fit within a user interface. The trend graph 50*a-d* may be interchangeable. The larger trend graph 50*a* can be replaced with one of smaller trend graphs 50*b-c*. The larger trend graph 50*a* can be minimized and exchanged with one of the smaller trend graphs 50*b-d*. In some embodiment the trend graphs can change position based on the occurrence of an event. For example, in if an alarm is triggered in one of the trend graphs 50*b-d*, trend graph 50*a* could be replaced with the alarming parameter by the patient monitoring system.

The health indicators illustrated in the user interface 100 can have ranges and thresholds to help evaluate the health and wellness of the patient. A range can have one or more thresholds. Some physiological parameters may have upper thresholds and lower thresholds, while other parameters may only have an upper threshold or a lower threshold. The thresholds can be useful in tracking and monitoring a patient's health. Some physiological parameters can have a single threshold to determine whether the patient is in a healthy or unhealthy range. Some physiological parameters can have a plurality of thresholds that can be used to help evaluate the state of health of the patient. For example, a blood pressure measurement can identify different stages of hypertension, as illustrated in indicator 30*b*. The ranges and thresholds can be adjusted based on the physiological parameter being monitored. For example, a SpO2 health indicator, such as 10*b*, can have only a lower threshold, whereas a heart rate indicator, such as 10*a*, can have both an upper and a lower threshold.

The ranges and thresholds for each physiological parameter can be based on typical or expected values for a patient. The ranges and thresholds can be based on gender, age, height, weight, and other patient data. For example, females can have different ranges and thresholds than males. In some embodiments, a medical practitioner can determine ranges and thresholds for each parameter. In some embodiments, the patient monitoring system can determine the ranges and thresholds based at least in part on patient information provided to the system. A user can provide the system with information about the patient, such as gender, age, height, weight, medical history, and the like. The system can analyze the information and determine appropriate ranges and thresholds for the patient. In some embodiments, the ranges and thresholds can be determined by referencing one or more predefined look-up tables. In some embodiments, the ranges and thresholds can be calculated using one or more algorithms. In some embodiments the user can modify the ranges and thresholds after the system has completed a determination of the ranges and thresholds.

Figure 4:
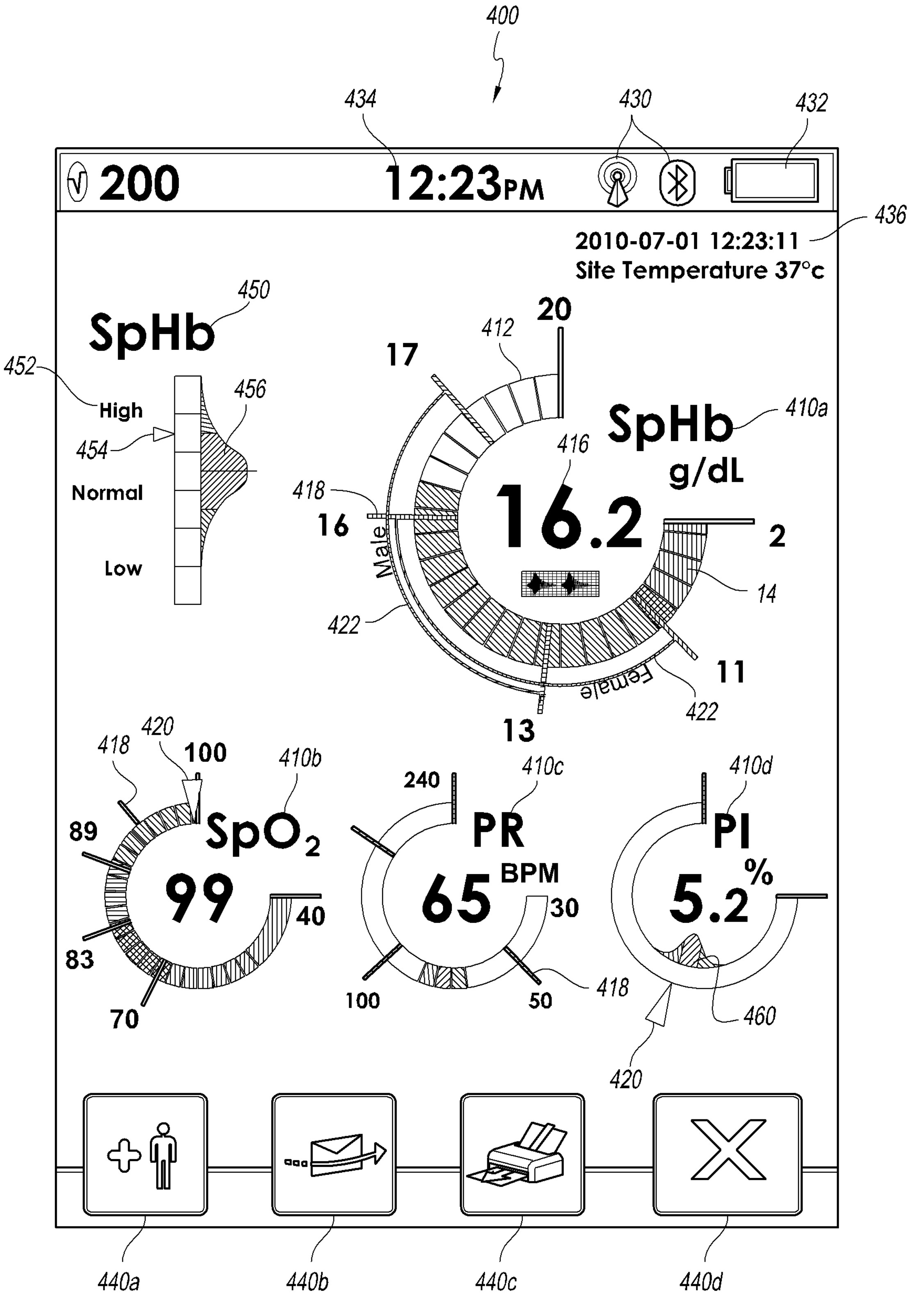
FIG. 4 is another embodiment of a user interface showing a plurality of health indicators.

When a threshold is met or exceeded, the system may be programmed to trigger an event. The event may be an alarm, an on-screen notification, an audible alarm, an electronic message sent to a health practitioner, or other user-specified event. In some embodiments, the user interface can change to indicate that an event has been triggered. For example, the indicators can change color, the indicator can flash, the indicator can increase in size, the indicator can switch to a different position on the display, or other change to the user interface to indicate that an event has been triggered. In some embodiments the triggered indicator can replace another more prominent indicator on the display The health indicators can display the range and threshold information in a number of ways. The indicators can have marks, text, or other indication on the health indicator that identifies threshold. Other descriptors or annotations can be placed on the health indicators to identify ranges and or thresholds, which could be based on gender, age, or other information about the patient. The indicators can have numeric values associated with the descriptors. In some embodiments, no numeric values are associated with the indicators, such as the indicator 450 in FIG. 4. The indicators can have descriptors that indicate maximum and minimum thresholds for the physiological parameter, such as descriptors 422, described in association with FIG. 4, showing minimum and maximums for males and females, or thresholds 58 in trend graph 50*a*. A practitioner can use the ranges and thresholds to assess the severity of the physiological parameter levels.

In some embodiments, the ranges can be identified by color patterns, and the thresholds are identified by changes to the color pattern. This can aid the less educated or foreign language speakers to identify problems quickly. The color of the health indicator bars can indicate patient condition, such as normal, deteriorating, severe, and critical. For example, green can indicate a normal physiological signal, yellow can indicate a deteriorating condition, orange can indicate a severe condition, and red can indicate a critical condition. A health practitioner can quickly assess a patient's health by evaluating the color of each health indicator. This can be particularly helpful for when a health practitioner sees a new or unfamiliar patient. The patient monitoring system can use ranges and thresholds in all of the indicators.

Figure 2:
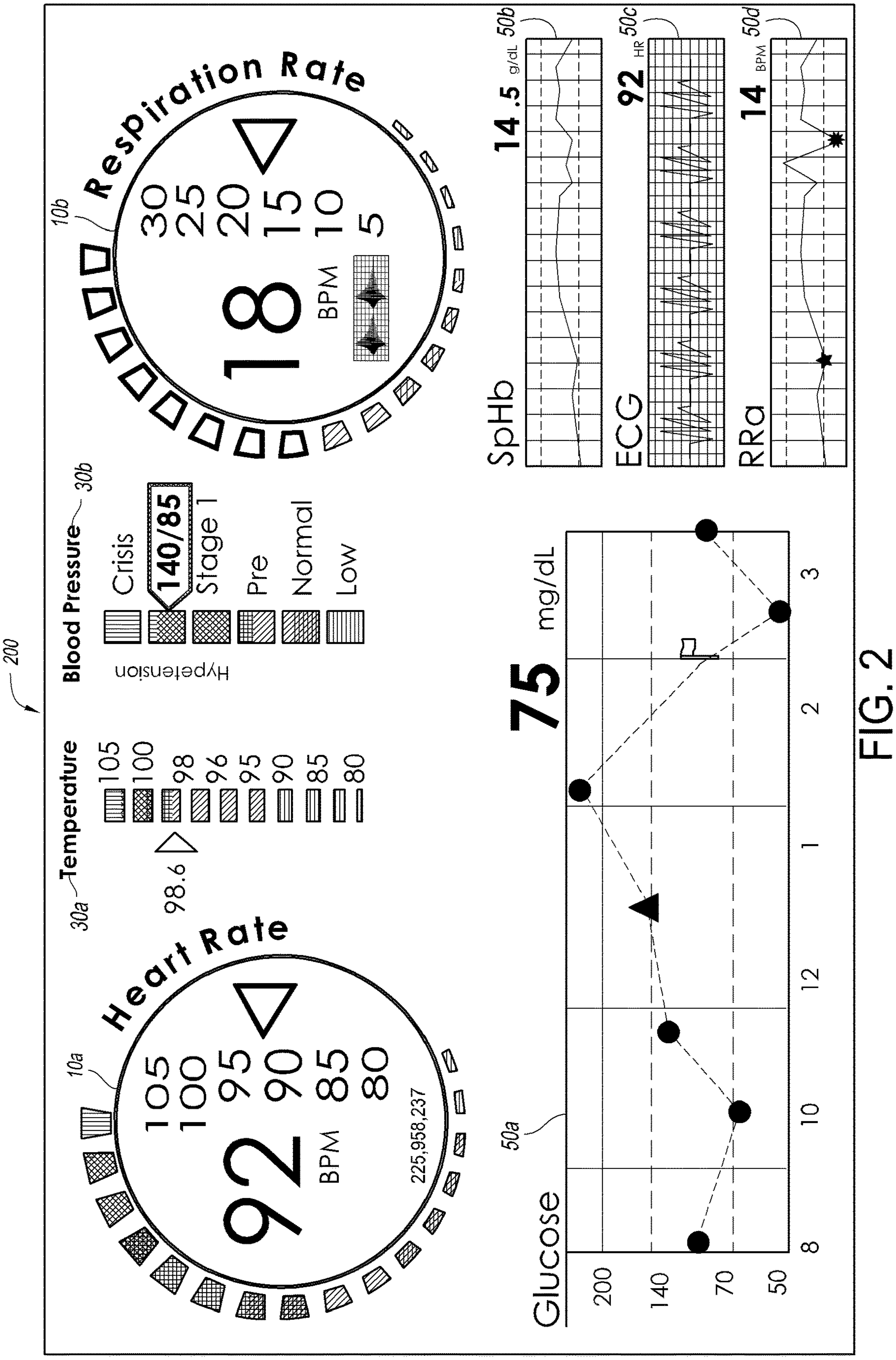
FIG. 2 is another embodiment of a configuration of user interface showing a plurality of health indicators.

FIG. 2 illustrates another configuration of the health indicators illustrated in FIG. 1.

Figure 3:
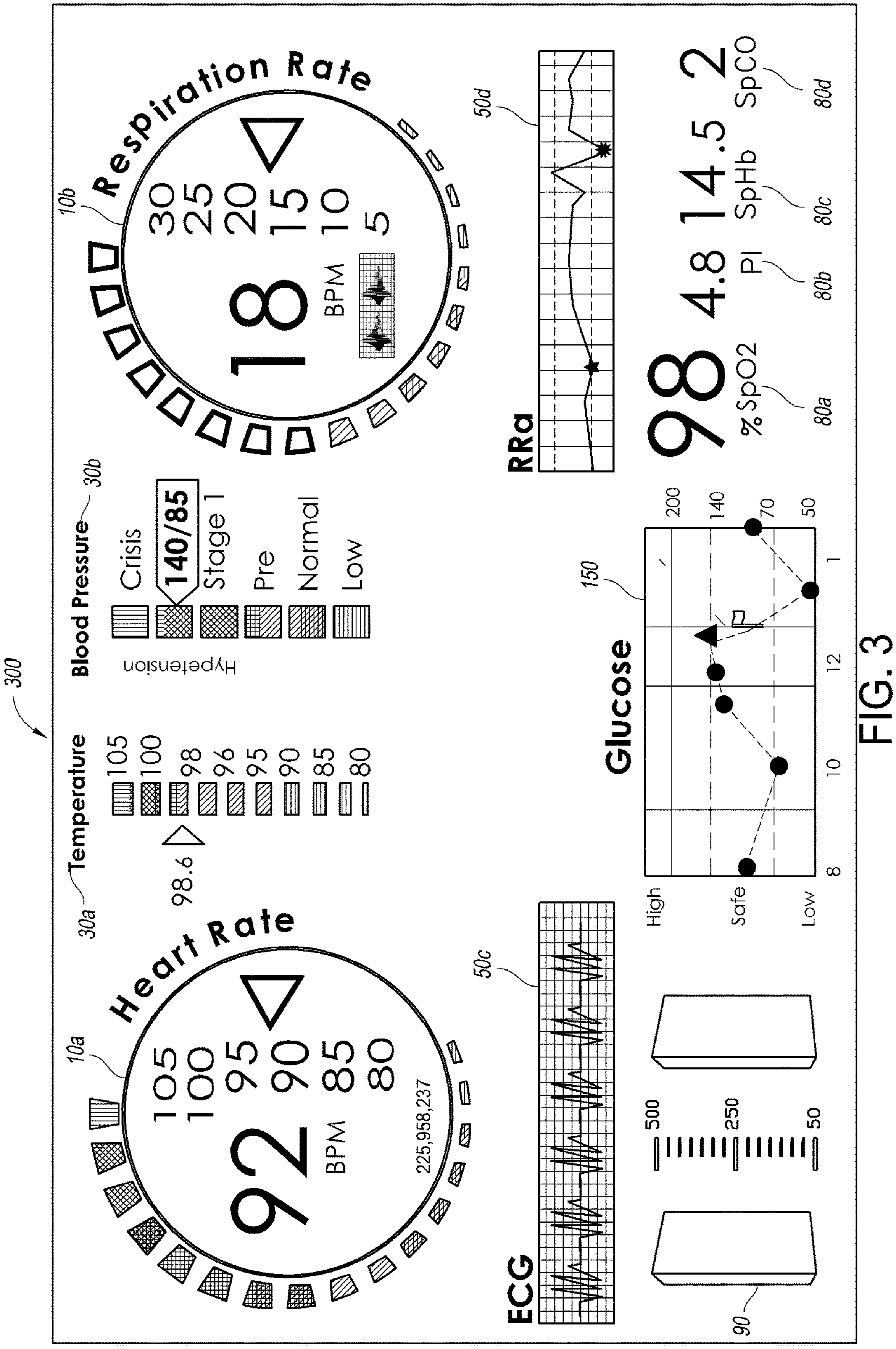
FIG. 3 is another embodiment of a configuration of a user interface showing a plurality of health indicators.

FIG. 3 is another embodiment of a configuration of a user interface 300 that shows a plurality of health indicators for heart rate 10*a*, respiration rate 10*b*, temperature 30*a*, blood pressure 30*b*, glucose 150, ECG 50*c*, and respiration rate (RRa) 50*d*, oxygen saturation (% SpO2) 80*a*, perfusion index (PI) 80*b*, total hemoglobin (SpHb) 80*c*, carboxyhemoglobin (SpCO) 80*d*, and bar indicators 90. The heart rate 10*a*, respiration rate 10*b*, temperature 30*a*, blood pressure 30*b*, indicators are substantially the same as the indicators described in association with FIG. 1. In this embodiment of the user interface 300, the indicators have been positioned and sized differently than those in FIG. 1.

The user interface 300 illustrates another embodiment of a trend chart 150. The trend chart 150 is substantially similar to the trend chart 50*a*. The trend chart 150 has upper and lower thresholds forming three regions, identified by descriptors on the left side of the chart. Measurement values above the upper threshold are "High," measurement values below the lower threshold are "Low," and measurement values between the upper and lower thresholds are "Safe." In this embodiment the current measurement value is displayed by the lines on the trend graph and not by a numerical indicator.

The user interface 300 illustrates another embodiment of a vertical bar indicator 90. The measurement value is illustrated by the height of the indicator 90. The width of the indicators 90 can indicate the amount of data being used and the upper and lower bounds next to the indicators 90 can indicate specific measurement values. In some embodiments, the indicator can change color to indicate the criticality of the measurement value. For example the indicator can be red if the value exceeds a threshold.

The user interface 300 also includes digital indicators for oxygen saturation (% SpO2) 80*a*, perfusion index (PI) 80*b*, total hemoglobin (SpHb) 80*c*, and carboxyhemoglobin (SpCO) 80*d*. The indicators 80*a-d* display the current values of the various physiological parameters. The indicator 80*a* is larger than the other indicators 80*b-d*. The indicators can be configured to position the indicator that is most critical in the position of indicator 80*a*. The measured value can be colored to indicate the level of patient wellness. In some embodiments the indicators can illuminate or flash based on the occurrence of an event, such as an alarm.

FIG. 4 illustrates another embodiment of a user interface 400. The user interface 400 shows a plurality of health indicators, including total hemoglobin (SpHb), circular indicator 410*a* and Gaussian indicator 450, oxygen saturation (SpO2) 410*b*, heart rate (PR) 410*c*, and perfusion index (PI) 410*d*. The user interface 400 also includes network information 430, power, battery power 432, time 434, patient site information 436, and additional program specific commands 440*a-d*.

The user interface 400 illustrates another embodiment of circular indicators 410*a-d*. The circular indicators 410*a-d* have a gauge 412 arranged circumferentially about a numeric value 416. In this embodiment, a quarter of the indicator is used to display the name and units of the physiological parameter and ¾ of the indicator is the gauge 412. The gauge 412 can illuminate to correspond to the current sensor measurement. The gauge can include one or more blocks, as illustrated in 410*a-c*. The circular indicator 410*a* can have a measurement pointer 420 that identifies the current measurement. In some embodiments the gauge 412 has a color pattern associated with the health indicator reading.

The circular indicators 410*a-d* can have one or more reference points 418 at specific positions about the indicator. The reference points 418 can be lines, points, or other indicators that can indicate ranges and thresholds of the physiological parameter. In some embodiments, no values are displayed on the gauge, such as 410*d*. In some embodiments, reference point 418 can have numeric values, such as indicators 410*a-c*.

The indicators can have descriptors or reference information 422 on or about the gauge 412. The descriptors 422 can indicate wellness thresholds or other information related to the health indicator. The health indicator 410*a* has descriptors 422 showing ranges for male and female patients. In some embodiments, the descriptors 422 can illustrate ranges for other classifications such as age (e.g., children, elderly, etc.), fitness level (e.g., athlete), or other classification. In some embodiments the descriptors 422 can indicate a maximum threshold and/or a minimum threshold.

The circular indicators 410*a-d* may be interchangeable. The larger indicator 410*a* can be replaced with one of smaller indicators 410*b-d*. The larger indicator 410*a* can be reduced in size and the other indicator can be increased in size. In some embodiments the indicator 450 can also be replaced when the indicator 410*a* is replaced. In some embodiment the indicators 410*a-d* can change position based on the occurrence of an event. For example, if an alarm is triggered in one of the indicators 410*b-d*, indicator 410*a* could be replaced with the alarming parameter by the patient monitoring system.

In some embodiments the indicators 410*a-d* can illustrate trends based on the color and intensity of the gauge 412. In one embodiment the highest intensity portion of the gauge 412 can indicate the most recent measurement with the intensity reducing for previous measurements. The intensity can be varied by the luminescence and/or the shade of color of the gauge 412. The intensity can be varied based on time or the number of measurements. For example, an indicator may be configured to show the last four measurements, with each measurement having a different intensity. In another example, the indicator may show measurements over the previous hour with a representative measurement shown for every ten minute period having a different intensity. In some embodiments the intensity can be increased to show which value has the most measurements, similar to a Gaussian trend. In some embodiments the indicator can have discrete intensity levels and/or colors that indicate timing of the measurements. For example the indicator 410*c* has three blocks that can represent different intensities and/or colors. In some embodiments the gauge can use the color associated with the severity of the measurement, for example if the measurement is a healthy measurement, that portion of the gauge can be a shade of green, whereas if it is an unhealthy measurement, that portion of the gauge can be a shade of red.

The user interface 400 also includes the indicator 450 configured to illustrate a distribution of measurements over a period of time, such as a Gaussian trend. The Gaussian trend indicator can have descriptors 452, an indicator 454, a distribution graph 456. The indicator 454 can indicate the current measurement. The distribution graph 456 indicates the amount of time spent at each measurement relative to other measurements. The distribution graph can be updated with each measurement. In some embodiments, the distribution graph can calculate the distribution for an indefinite period of time. In some embodiments the distribution can be a rolling window of time that only monitors distribution for a set amount of time going backwards. For example, the distribution graph 456 could show the distribution of measurements for 30 minutes, one hour, 6 hours, 24 hours or any appropriate length of time. An example of a Gaussian trend graph 460 being used in conjunction with a circular indicator is illustrated in indicator 410*d*. An embodiment of a time distribution graph, such as a Gaussian trend, can be used in conjunction with all indicators and parameters discussed herein.

The user interface 400 also includes exemplary program specific commands 440*a-d*. In this embodiment, the program specific commands include paging a medical practitioner 440*a*, sending the user interface information via electronic messaging 440*b*, printing 440*c*, and exiting out of the interface 440*d*.

FIG. 5 illustrates an embodiment of a patient monitoring system 500. In the depicted embodiment, the patient monitoring system 500 includes a display 520 and a monitoring device 500, which includes a finger clip sensor 501 connected to a monitor 509 via a cable 512. The patient monitoring system display 520 is configured to display a user interface 522, such as one of the user interfaces described in association with FIGS. 1-4.

In the embodiment shown, the monitor 509 includes a display 510. The monitor 509 can advantageously include electronic processing, signal processing, and data storage devices capable of receiving signal data from said sensor 501, processing the signal data to determine one or more output measurement values indicative of one or more physiological parameters of a monitored patient, and displaying the measurement values, trends of the measurement values, combinations of measurement values, and the like.

The monitor 509 can also include other components, such as a speaker, power button, removable storage or memory (e.g., a flash card slot), an AC power port, one or more control buttons 508 and one or more network interfaces, such as a universal serial bus interface or an Ethernet port. The display 510 can have a user interface displaying one or more health indicators, such as the indicators described herein. The cable 512 connecting the sensor 501 and the monitor 509 can be implemented using one or more wires, optical fiber, flex circuits, or the like.

The embodiments set forth above are illustrative of inventive principles and features, and these principles may be applied to patient monitoring systems that have different user interfaces or health indicators that do not match the embodiments of the patient monitoring system illustrated in the Figures. For example, the user interfaces may have different or additional health indicators. The health indicators may have different sizes and shapes, or different color patterns. As such, the principles and features discussed herein can be applied in embodiments of various shapes, sizes and configurations.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. Accordingly, Applicants contemplate that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A patient monitoring system, comprising:

at least one physiological sensor including a first light emitter, a second light emitter, and a detector, wherein the at least one physiological sensor is configured to measure at least one physiological signal from a patient, wherein the at least one physiological sensor includes at least one of a pulse oximeter, a heart rate monitor, a respiratory monitor, or a thermometer;

a display; and a processor comprising computer-executable instructions that, when executed, cause the processor to:

generate a user interface for the display, the user interface including at least one first health indicator, the at least one first health indicator comprising a circumferential gauge including a plurality of indicator elements indicative of signal values of the at least one physiological signal, wherein the plurality of indicator elements include;

(i) a circular graphical indicator element that is indicative of a current measurement value of the at least one physiological signal, (ii) a plurality of reference lines positioned around the circumference of the circular graphical indicator element to indicate different ranges of the signal values of the at least one physiological signal, and (iii) descriptor indicators indicative of the different ranges of the signal values of the at least one physiological signal for groups of patients grouped according to a patient classification determined by the processor;

receive patient information;

receive the at least one physiological signal from the at least one physiological sensor;

determine at least one threshold for the at least one health indicator based at least in part on the patient information;

set a first and second range of values for the at least one first health indicator based on the at least one threshold, wherein the first range of values corresponds to a first range of physiological signals from the patient; and wherein the second range of values corresponds to a second range of physiological signals from the patient;

compare the current measurement value to the first and second range of values;

generate a first visual output of the circumferential gauge when the current measurement value is within the first range of values;

generate a second visual output of the circumferential gauge when the current measurement value is within the second range of values; and output an alarm signal when the current measurement value moves from the first range of values to the second range of values.

2. The patient monitoring system of claim 1, wherein the first visual output is a first color displayed on the at least one first health indicator and the second visual output is a second color displayed on the at least one first health indicator.

3. The patient monitoring system of claim 1, wherein the patient monitoring system is configured to communicate the signal value with a mobile device.

4. The patient monitoring system of claim 1, wherein the patient information is at least one of age, gender, height, or weight.

5. The patient monitoring system of claim 1, wherein the patient information is information associated with a medical history of the patient.

6. The patient monitoring system of claim 1, wherein the plurality of indicator elements further comprise a numeric value of the signal value.

7. The patient monitoring system of claim 1, wherein the at least one physiological sensor is configured to measure at least one of glucose, blood pressure, pulse rate, respiration rate, oxygen saturation, total hemoglobin, carboxyhemoglobin, methemoglobin, perfusion index, or temperature.

8. The patient monitoring system of claim 1, wherein the user interface includes at least one second health indicator, the at least one second health indicator comprising an elongate bar indicator, wherein the processor is further configured to:

determine a distribution of signal values of a second physiological signal over a first time period based at least in part on the patient information; and generate and output for display, in real time and in conjunction with the current measurement value and the at least one first health indicator, a real-time distribution graph of signal values of the second physiological signal over the first time period, wherein the real-time distribution graph is displayed adjacent to a portion of the elongate bar indicator.

9. The patient monitoring system of claim 8, wherein the first time period is an indefinite time period.

10. The patient monitoring system of claim 8, wherein the first time period is a rolling window of time having a defined time period.

11. The patient monitoring system of claim 1, wherein the processor is further configured to calculate a third range of values for the at least one first health indicator, wherein the third range of values corresponds to a third range of physiological signals from the patient.

12. The patient monitoring system of claim 11, wherein the first range of values, the second range of values, and the third range of values do not overlap.

13. The patient monitoring system of claim 11, wherein the first range of values corresponds to a healthy patient condition, the second range of values corresponds to an unhealthy patient condition, and the third range of values corresponds to an intermediate patient condition.

14. The patient monitoring system of claim 1, wherein the patient classification comprises gender, age group, or fitness level.

15. The patient monitoring system of claim 1, wherein the descriptor indicator at least partially overlap with the graphical indicator element.

16. The patient monitoring system of claim 8, wherein the real-time distribution graph illustrates a Gaussian trend of the at least one physiological signal.

17. The patient monitoring system of claim 16, wherein the real-time distribution graph is continuously updated with each measurement value of the second physiological signal.

18. The patient monitoring system of claim 16, wherein the first visual output or the second visual output is displayed in conjunction with the real-time distribution graph.

* * * * *